United States Patent
Baba et al.

(10) Patent No.: US 11,807,602 B2
(45) Date of Patent: Nov. 7, 2023

(54) PROCESSES FOR PREPARING A 3-ISOPROPENYL-6-HEPTENAL COMPOUND AND A 6-ISOPROPENYL-3-METHYL-3,9-DECADIENYL CARBOXYLATE COMPOUND, AND AN INTERMEDIATE THEREFOR

(71) Applicant: Shin-Etsu Chemical Co., Ltd., Tokyo (JP)

(72) Inventors: Akihiro Baba, Joetsu (JP); Takeshi Kinsho, Joetsu (JP); Naoki Ishibashi, Joetsu (JP); Yusuke Nagae, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/543,877

(22) Filed: Dec. 7, 2021

(65) Prior Publication Data

US 2022/0185763 A1    Jun. 16, 2022

(30) Foreign Application Priority Data

Dec. 10, 2020  (JP) .................................. 2020-205403

(51) Int. Cl.

| | |
|---|---|
| C07C 45/41 | (2006.01) |
| C07C 67/27 | (2006.01) |
| C07C 69/587 | (2006.01) |
| C07C 67/08 | (2006.01) |
| C07C 67/475 | (2006.01) |

(52) U.S. Cl.
CPC ............ *C07C 69/587* (2013.01); *C07C 45/41* (2013.01); *C07C 67/08* (2013.01); *C07C 67/27* (2013.01); *C07C 67/475* (2013.01)

(58) Field of Classification Search
CPC ....... C07C 69/587; C07C 67/08; C07C 67/27; C07C 67/475; C07C 45/41
See application file for complete search history.

(56) References Cited

U.S. PATENT DOCUMENTS 4,201,874 A * 5/1980 Anderson ................ C07C 67/08
562/598
2011/0172304 A1   7/2011 Ishibashi et al.

FOREIGN PATENT DOCUMENTS

JP          2011144114 A      7/2011

OTHER PUBLICATIONS

Kher, S.M. et al., A short and formal synthesis of California Red Scale Pheromone, Synthetic Communications, vol. 20, issue 4, pp. 495-501 (Year: 1990).*

Oppolzer, W. et al., Asymmetric additions of 1-alkenylcopper reagents to chiral enoates: Enantioselective synthesis of California Red Scale Pheromone, Tetrahedron Letters, vol. 27, No. 10, pp. 1139-1140 (Year: 1986).*
Song, I.J. et al., New method for synthesis of aldehydes from esters by sodium diisobutyl-t-butoxyaluminum hydride, Chemistry Letters, vol. 36, No. 7, pp. 886-887 (Year: 2007).*
Gieselmann et al. "Responses of Male California Red Scale to Sex Pheromone Isomers" Journal of Insect Physiology, 263:179-182 (1980).
Heath et al. "Sex Pheromone of the White Peach Scale: Highly Stereoselective Synthesis of the Stereoisomers of Pentagonol Propionate" Journal of Organic Chemistry, 45(14):2910-2912 (1980).
Roelofs et al. "Identification of the California Red Scale Sex Pheromone" Journal of Chemical Ecology, 4:211-224 (1978).
Schlosser et al. "SCOOPY and Oxirane Reactions: alpha-Lithio-Ylides vs. Conventional Ylides" Chimia, 37:10-11 (1983).
Extended European Search Report corresponding to European Patent Application No. 21212942.3 (12 pages), dated May 10, 2022.
Kher et al. "A Shot and Formal Synthesis of California Red Scale Pheromone" Synthetic Communications, 20(4):495-501 (1990).
Oppolzer et al. "Asymmetric Additions of 1-Alkenylcopper Reagents to Chiral Enoates: Enantioselective Synthesis of California Red Scale Pheromone" Tetrahedron Letters, 27(10):1139-1140 (1986).

* cited by examiner

*Primary Examiner* — Yate' K Cutliff
(74) *Attorney, Agent, or Firm* — Myers Bigel, P.A.

(57) ABSTRACT

The present invention relates to a process for preparing a 3-isopropenyl-6-heptenal compound of the following formula (2): wherein $R^1$ represents a hydrogen atom or a methyl group, the process comprising: subjecting a 3-isopropenyl-6-heptenoate ester compound of the following formula (1): wherein $R^1$ is as defined above, and $R^2$ represents a monovalent hydrocarbon group having 1 to 10 carbon atoms, to a reduction reaction with a reducing agent to form the 3-isopropenyl-6-heptenal compound (2).

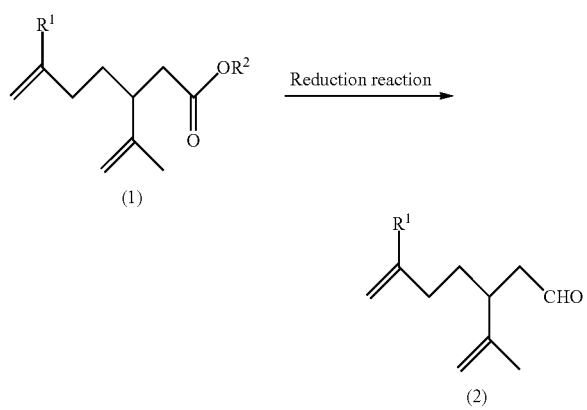

12 Claims, No Drawings

PROCESSES FOR PREPARING A 3-ISOPROPENYL-6-HEPTENAL COMPOUND AND A 6-ISOPROPENYL-3-METHYL-3,9-DECADIENYL CARBOXYLATE COMPOUND, AND AN INTERMEDIATE THEREFOR

TECHNICAL FIELD

The present invention relates to processes for preparing a 3-isopropenyl-6-heptenal compound and a 6-isopropenyl-3-methyl-3,9-decadienyl carboxylate compound, and an intermediate therefor, i.e., 3-isopropenyl-6-methyl-6-heptenoate ester compound, and a process for preparing the intermediate.

BACKGROUND ART

Insect sex pheromones are biologically active substances which are usually borne by females to attract males, and exhibit a high attracting activity in a small amount. Sex pheromones are widely utilized as a means for forecasting outbreaks of pests and confirming geographic spread (invasion into a specific area), and also as a means for controlling pests. Widely used methods for controlling pests include a mass trapping method, a lure-and-kill or attract-and-kill method, a lure-and-infect or attract-and-infect method, and a mating disruption method. A naturally occurring sex pheromone can be extracted from an insect individual only in a trace amount. Therefore, it is difficult to use a naturally occurring sex pheromone for a mating disruption method. Before practical use of a sex pheromone, it is highly required to artificially and industrially produce a sufficient amount of a sex pheromone for basic research and also for applications.

California red scale (scientific name: *Aonidiella aurantii*) is a pest that has spread widely throughout the world to infest citrus. (3Z,6R)-6-Isopropenyl-3-methyl-3,9-decadienyl acetate is reported as a sex pheromone of California red scale (Non-Patent Literature 1 listed below). 6-Isopropenyl-3-methyl-3,9-decadienyl acetate includes four isomers: (3Z,6R)-6-isopropenyl-3-methyl-3,9-decadienyl acetate, (3E,6R)-6-isopropenyl-3-methyl-3,9-decadienyl acetate, (3Z,6S)-6-isopropenyl-3-methyl-3,9-decadienyl acetate, and (3E,6S)-6-isopropenyl-3-methyl-3,9-decadienyl acetate. It is reported that California red scale is attracted also by a mixture of these four isomers (Non-Patent Literature 1).

A process for preparing (3Z,6R)-6-isopropenyl-3-methyl-3,9-decadienyl acetate is reported, wherein the process comprises first nine steps including an oxidation reaction of (S)-(+)-carvone, which is a starting material, with hydrogen peroxide to obtain (R)-3-isopropenyl-6-heptenal; and then three steps including a Wittig reaction; and separation of the product by gas-liquid chromatography (GLC) to obtain (3Z,6R)-6-isopropenyl-3-methyl-3,9-decadienyl acetate (Non-Patent Literature 2 listed below).

White peach scale (scientific name: *Pseudaulacaspis pentagona*) is a pest that has spread widely throughout the world to infest fruits, such as peaches, and tea. (3Z,6R)-6-Isopropenyl-3,9-dimethyl-3,9-decadienyl propionate is reported as a sex pheromone of White peach scale (Non-Patent Literature 3 listed below). 6-Isopropenyl-3,9-dimethyl-3,9-decadienyl propionate includes four isomers: (3Z,6R)-6-isopropenyl-3,9-dimethyl-3,9-decadienyl propionate, (3E,6R)-6-isopropenyl-3,9-dimethyl-3,9-decadienyl propionate, (3Z,6S)-6-isopropenyl-3,9-dimethyl-3,9-decadienyl propionate, and (3E,6S)-6-isopropenyl-3,9-dimethyl-3,9-decadienyl propionate. White peach scale is attracted also by a mixture of its sex pheromone, (3Z,6R)-6-isopropenyl-3,9-dimethyl-3,9-decadienyl propionate, and an isomer thereof, (3E,6R)-6-isopropenyl-3,9-dimethyl-3,9-decadienyl propionate (Patent Literature 1 listed below).

A process for preparing (3Z,6R)-6-isopropenyl-3,9-dimethyl-3,9-decadienyl propionate is reported, wherein the process comprises, for example, the following steps in the following order: carrying out ozonolysis of (R)-(+)-limonene; subjecting the product to a Wittig reaction followed by a hydrolysis of the resulting acetal to obtain (R)-3-isopropenyl-6-methyl-6-heptenal; and subjecting the product to four-carbon homologation including a Wittig reaction, followed by propionylation to obtain (3Z,6R)-6-isopropenyl-3,9-dimethyl-3,9-decadienyl propionate (Non-Patent Literature 3 listed below).

LIST OF THE LITERATURES

Patent Literature

[Patent Literature 1] Japanese Patent Application Laid-Open No. 2011-144114

Non-Patent Literatures

[Non-Patent Literature 1] M. J. Gieselmann et al., J. Insect. Physiol. 26, 179 (1980)
[Non-Patent Literature 2] W. Roelofs et al., J. Chem. Ecol., Vol. 4, No. 2, 211 (1978)
[Non-Patent Literature 3] R. R. Heath et al., J. Org. Chem. 45, 2910 (1980)
[Non-Patent Literature 4] M. Schlosser et al., CHIMIA 37, 10 (1983)

Problems to be Solved by the Invention

In the process described in Non-Patent Literature 2, an oxidation reaction of (S)-(+)-carvone is carried out with hydrogen peroxide. This oxidation reaction may cause explosion and, therefore, is industrially less feasible. Moreover, the process requires nine steps to obtain an intermediate, (R)-3-isopropenyl-6-heptenal from the starting material, (S)-(+)-carvone, resulting in a total yield as low as 12%. Moreover, the total process for preparing (R)-6-isopropenyl-3-methyl-3,9-decadienyl acetate from the starting material, (S)-(+)-carvone, gives a total yield as low as 5.3%.

In the process described in Non-Patent Literature 3, ozone, which is corrosive and highly poisonous, is used in an oxidation reaction of (R)-(+)-limonene. This oxidation reaction is, therefore, industrially less feasible.

Thus, the aforesaid known processes are very difficult to be used for industrially preparing a sufficient amounts of 6-isopropenyl-3-methyl-3,9-decadienyl acetate or 6-isopropenyl-3,9-dimethyl-3,9-decadienyl propionate.

SUMMARY OF THE INVENTION

The present invention has been made in these circumstances, and aims to provide a process for efficiently and industrially preparing 6-isopropenyl-3-methyl-3,9-decadienyl carboxylate compounds such as 6-isopropenyl-3-methyl-3,9-decadienyl acetate and 6-isopropenyl-3,9-dimethyl-3,9-decadienyl propionate, without oxidation reaction, in a sufficient amount for biological or agricultural activity tests and/or for practical application.

The present invention also aims to provide processes for preparing 3-isopropenyl-6-heptenal and 3-isopropenyl-6- methyl-6-heptenal, which are useful intermediates in the preparation of the compounds described above.

The present invention further aims to provide a 3-isopropenyl-6-methyl-6-heptenoate ester compound, which is a useful intermediate in the preparation of 3-isopropenyl-6-methyl-6-heptenal.

As a result of the intensive researches to solve the problems, the present inventors have found that a 3-isopropenyl-6-heptenoate ester compound is subjected to a reduction reaction with a reducing agent to form a 3-isopropenyl-6-heptenal compound. The present inventors have also found that a 3-isopropenyl-6-heptenal compound may be used as an intermediate to industrially prepare 6-isopropenyl-3-methyl-3,9-decadienyl acetate and 6-isopropenyl-3,9-dimethyl-3,9-decadienyl propionate. The present inventors have further found that a 3-isopropenyl-6-heptenoate ester compound may be efficiently and industrially prepared, without any oxidation reaction, by carrying out a Wittig reaction between a 4-pentenyltriphenylphosphonium halide compound and a 2-propanone compound having a protected hydroxyl group, followed by removal of the protective group, and then a Johnson-Claisen rearrangement. Thus, the present invention has been invented.

One aspect of the present invention provides a process for preparing a 3-isopropenyl-6-heptenal compound of the following formula (2):

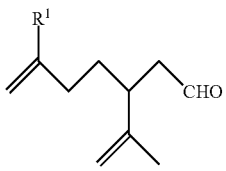

(2)

wherein $R^1$ represents a hydrogen atom or a methyl group, the process comprising:

subjecting a 3-isopropenyl-6-heptenoate ester compound of the following formula (1):

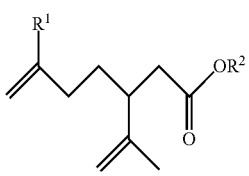

(1)

wherein $R^1$ is as defined above, and $R^2$ represents a monovalent hydrocarbon group having 1 to 10 carbon atoms, to a reduction reaction with a reducing agent to form the 3-isopropenyl-6-heptenal compound (2).

Another aspect of the present invention provides a process for preparing a 6-isopropenyl-3-methyl-3,9-decadienyl carboxylate compound of the following formula (4):

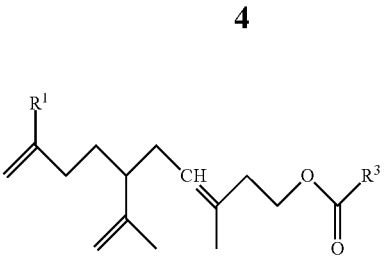

(4)

wherein $R^1$ represents a hydrogen atom or a methyl group, and $R^3$ represents a hydrogen atom or a monovalent hydrocarbon group having 1 to 10 carbon atoms, the process comprising:

the aforesaid process for preparing the 3-isopropenyl-6-heptenal compound (2);

subjecting the 3-isopropenyl-6-heptenal compound (2) thus obtained to four-carbon homologation reaction including a Wittig reaction, using an ethyltriphenylphosphonium halide compound and ethylene oxide to form a 6-isopropenyl-3-methyl-3,9-decadienol compound of the following formula (3):

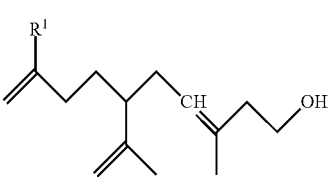

(3)

wherein $R^1$ is as defined above; and subjecting the 6-isopropenyl-3-methyl-3,9-decadienol compound (3) thus obtained to an esterification reaction to form the 6-isopropenyl-3-methyl-3,9-decadienyl carboxylate compound (4).

Another aspect of the present invention provides a process for preparing a 3-isopropenyl-6-heptenoate ester compound (1), the process comprising:

subjecting a 4-pentenyltriphenylphosphonium halide compound of the following formula (5):

(5)

wherein $R^1$ represents a hydrogen atom or a methyl group, Ph represents a phenyl group, and X represents a halogen atom, to a Wittig reaction with a 2-propanone compound of the following formula (6) having a protected hydroxyl group:

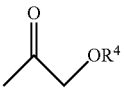

(6)

wherein $R^4$ represents a protective group for a hydroxyl group, to form a 2-methyl-2,6-heptadiene compound of the following formula (7) having a protected hydroxyl group at position 1:

(7)

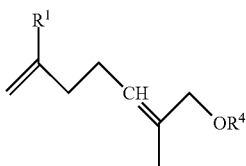

wherein R¹ and R⁴ are as defined above;

removing the protective group from the 2-methyl-2,6-heptadiene compound (7) having a protected hydroxyl group at position 1 to form a 2-methyl-2,6-heptadienol compound of the following formula (8)

(8)

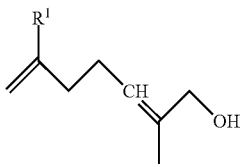

wherein R¹ is as defined above; and subjecting the 2-methyl-2,6-heptadienol compound (8) thus obtained to a Johnson-Claisen rearrangement with an orthoacetate ester compound to form the 3-isopropenyl-6-heptenoate ester compound (1).

Another aspect of the present invention provides a process for preparing a 3-isopropenyl-6-heptenal compound (2), the process comprising the aforesaid process for preparing the 3-isopropenyl-6-heptenoate ester compound (1) and subjecting the 3-isopropenyl-6-heptenoate ester compound (1) obtained to a reduction reaction with a reducing agent to form the 3-isopropenyl-6-heptenal compound (2).

Another aspect of the present invention provides a process for preparing a 6-isopropenyl-3-methyl-3,9-decadienyl carboxylate compound (4), the process comprising the aforesaid process for preparing a 3-isopropenyl-6-heptenoate ester compound (1) and steps of: subjecting the 3-isopropenyl-6-heptenoate ester compound (1) obtained from the preparation process to a reduction reaction with a reducing agent to form a 3-isopropenyl-6-heptenal compound (2); subjecting the 3-isopropenyl-6-heptenal compound (2) thus obtained to four-carbon homologation including a Wittig reaction, using an ethyltriphenylphosphonium halide compound and ethylene oxide to form a 6-isopropenyl-3-methyl-3,9-decadienol compound (3); and subjecting the 6-isopropenyl-3-methyl-3,9-decadienol compound (3) thus obtained to an esterification reaction to form the 6-isopropenyl-3-methyl-3,9-decadienyl carboxylate compound (4).

Another aspect of the present invention provides a process for preparing a 3-isopropenyl-6-heptenoate ester compound (1), the process comprising:

subjecting a 4-pentenyltriphenylphosphonium halide compound of the following formula (5):

(5)

wherein R¹ represents a hydrogen atom or a methyl group, Ph represents a phenyl group, and X represents a halogen atom, to a Wittig reaction with a 2-propanone compound of the following formula (6) having a protected hydroxyl group:

(6)

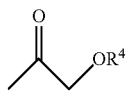

wherein R⁴ represents a protective group for a hydroxyl group;

followed by removal of the protective group to form a 2-methyl-2,6-heptadienol compound of the following formula (8):

(8)

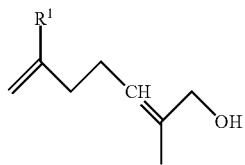

wherein R¹ is as defined above; and subjecting the 2-methyl-2,6-heptadienol compound (8) thus obtained to a Johnson-Claisen rearrangement with an orthoacetate ester compound to form the 3-isopropenyl-6-heptenoate ester compound (1).

Another aspect of the present invention provides a process for preparing a 3-isopropenyl-6-heptenal compound (2), the process comprising the process for preparing the 3-isopropenyl-6-heptenoate ester compound (1) and a step of subjecting the 3-isopropenyl-6-heptenoate ester compound (1) obtained from the preparation process to a reduction reaction with a reducing agent to form the 3-isopropenyl-6-heptenal compound (2).

Another aspect of the present invention provides a process for preparing a 6-isopropenyl-3-methyl-3,9-decadienyl carboxylate compound (4), the process comprising the process for preparing the 3-isopropenyl-6-heptenoate ester compound (1) and steps of: subjecting the 3-isopropenyl-6-heptenoate ester compound (1) obtained to a reduction reaction with a reducing agent to form the 3-isopropenyl-6-heptenal compound (2); subjecting the 3-isopropenyl-6-heptenal compound (2) thus obtained to four-carbon homologation including a Wittig reaction, using an ethyltriphenylphosphonium halide compound and ethylene oxide to form the 6-isopropenyl-3-methyl-3,9-decadienol compound (3); subjecting the 6-isopropenyl-3-methyl-3,9-decadienol compound (3) thus obtained to an esterification reaction to form the 6-isopropenyl-3-methyl-3,9-decadienyl carboxylate compound (4).

Another aspect of the present invention provides a 3-isopropenyl-6-methyl-6-heptenoate ester compound of the following general formula (1'):

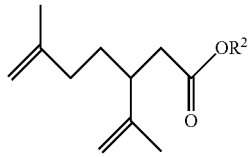

(1')

wherein R² represents a monovalent hydrocarbon group having 1 to 10 carbon atoms.

The present invention provides a process for efficiently and industrially preparing the 6-isopropenyl-3-methyl-3,9-decadienyl carboxylate compound, without an oxidation reaction that is industrially unfavorable in view of safety, economy, and environmental burden. The present invention also provides a process for preparing the 3-isopropenyl-6-heptenal compound, which is a useful intermediate in the preparation of a 6-isopropenyl-3-methyl-3,9-decadienyl carboxylate compound. The present invention further provides a 3-isopropenyl-6-methyl-6-heptenoate ester compound, which is a useful intermediate in the preparation of the 3-isopropenyl-6-methyl-6-heptenal compound.

DETAILED DESCRIPTION OF THE PREFERRED EMBODIMENTS

Embodiments of the present invention will be explained hereinafter in detail. It should be noted that the present invention is not limited to or by the embodiments. The intermediates, the reagents, and the target compounds represented by the chemical formulae may comprise isomers, such as structural isomers, and stereoisomers, such as enantiomers and diastereoisomers. Unless otherwise stated, the chemical formulae shall be interpreted to represent all of these isomers. The isomer may be either alone or in combination thereof.

The present inventors have contemplated, as described below, a plan for the synthesis of the 6-isopropenyl-3-methyl-3,9-decadienyl carboxylate compound (4), the 6-isopropenyl-3-methyl-3,9-decadienol compound (3), the 3-isopropenyl-6-heptenal compound (2), and the 3-isopropenyl-6-heptenoate ester compound (1), which are target compounds of the present invention.

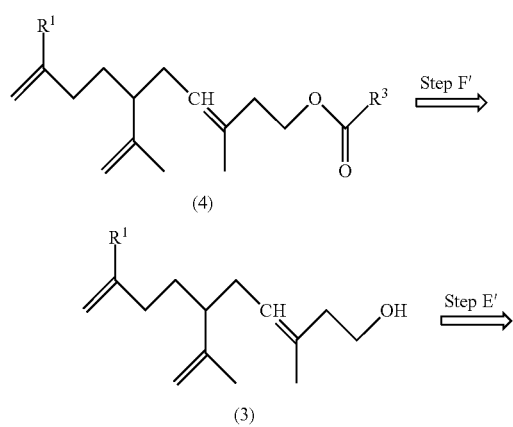

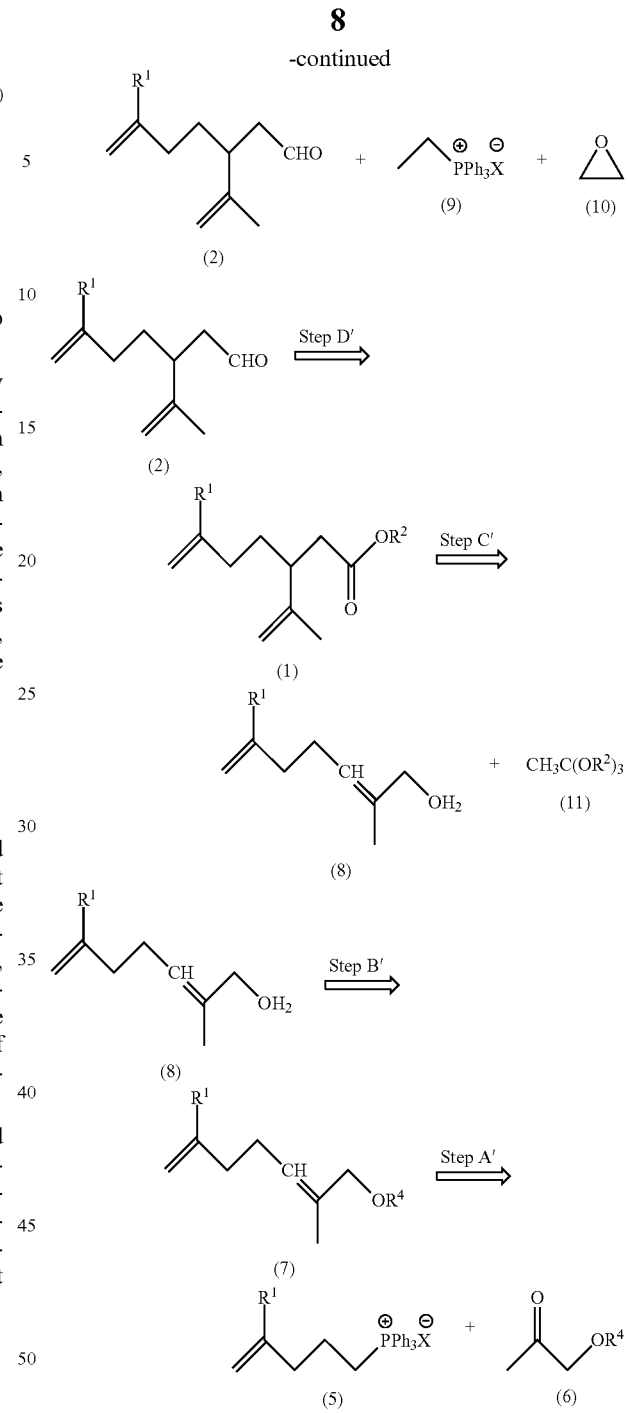

In reaction formulae of the retrosynthetic analysis shown above, the open arrows represent transforms in the retrosynthetic analysis. X represents a halogen atom, R¹ represents a hydrogen atom or a methyl group, R² represents a monovalent hydrocarbon group having 1 to 10 carbon atoms, R³ represents a hydrogen atom or a monovalent hydrocarbon group having 1 to 10 carbon atoms, and R⁴ represents a protective group for a hydroxyl group.

Step F'

The 6-isopropenyl-3-methyl-3,9-decadienyl carboxylate compound (4), which is a target compound of the present invention, is thought to be synthesized by subjecting the 6-isopropenyl-3-methyl-3,9-decadienol compound (3) to an esterification reaction.

The general formula (4) represents a (3Z,6R)-6-isopropenyl-3-methyl-3,9-decadienyl carboxylate compound of the following formula (4a), a (3E,6R)-6-isopropenyl-3-methyl-3,9-decadienyl carboxylate compound of the following formula (4b), a (3Z,6S)-6-isopropenyl-3-methyl-3,9-decadienyl carboxylate compound of the following formula (4c), or a (3E,6S)-6-isopropenyl-3-methyl-3,9-decadienyl carboxylate compound of the following formula (4d), or a combination thereof.

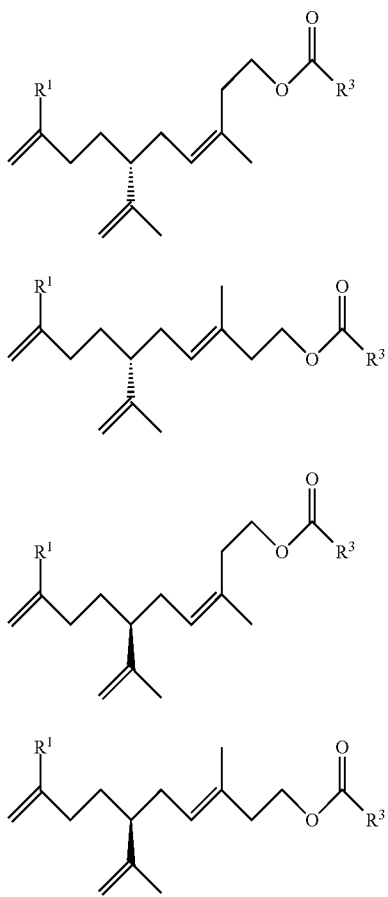

The general formula (3) represents a (3Z,6R)-6-isopropenyl-3-methyl-3,9-decadienol compound of the following formula (3a), a (3E,6R)-6-isopropenyl-3-methyl-3,9-decadienol compound of the following formula (3b), a (3Z,6S)-6-isopropenyl-3-methyl-3,9-decadienol compound of the following formula (3c), or a (3E,6S)-6-isopropenyl-3-methyl-3,9-decadienol compound of the following formula (3d), or a combination thereof.

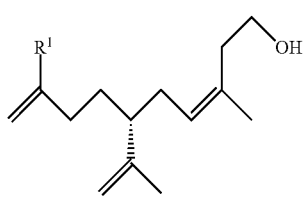

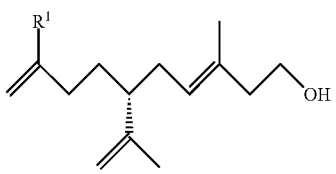

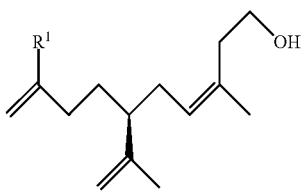

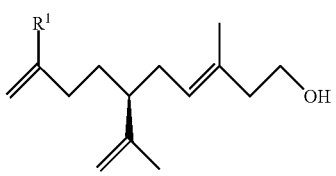

Step E'

The 6-isopropenyl-3-methyl-3,9-decadienol compound (3), which is another target compound of the present invention, is thought to be synthesized by subjecting the 3-isopropenyl-6-heptenal compound (2) to four-carbon homologation including a Wittig reaction, using an ethyltriphenylphosphonium halide compound of the formula (9) and ethylene oxide (10).

The general formula (2) represents an (R)-3-isopropenyl-6-heptenal compound of the following formula (2a) or an (S)-3-isopropenyl-6-heptenal compound of the following formula (2b), or a combination thereof.

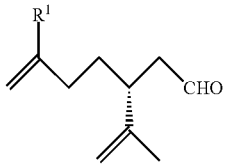

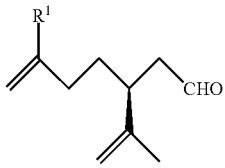

Step D'

The 3-isopropenyl-6-heptenal compound (2), which is another target compound of the present invention, is thought to be synthesized by selectively reducing an ester group of the 3-isopropenyl-6-heptenoate ester compound (1) into an aldehyde group, that is, subjecting the 3-isopropenyl-6-heptenoate ester compound (1) to a reduction reaction with a reducing agent.

The general formula (1) represents an (R)-3-isopropenyl-6-heptenoate ester compound of the following formula (1a) or an (S)-3-isopropenyl-6-heptenoate ester compound of the following formula (1b), or a combination thereof.

(1a)

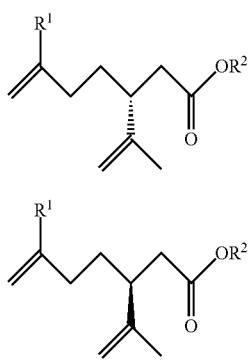

(1b)

Next, the present inventors have contemplated a plan for synthesis of the 3-isopropenyl-6-heptenoate ester compound (1), which is an intermediate to be used in the present invention.

Step C'

The 3-isopropenyl-6-heptenoate ester compound (1) is thought to be synthesized by subjecting the 2-methyl-2,6-heptadienol compound (8) to a Johnson-Claisen rearrangement with an orthoacetate ester compound (11).

The general formula (8) represents a (Z)-2-methyl-2,6-heptadienol compound of the following formula (8a) or an (E)-2-methyl-2,6-heptadienol compound of the following formula (8b), or a combination thereof.

(8a)

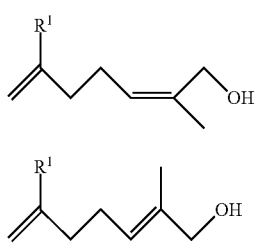

(8b)

Step B'

The 2-methyl-2,6-heptadienol compound (8) is thought to be synthesized by removing the protective group from the 2-methyl-2,6-heptadiene compound (7) having a protected hydroxyl group at position 1.

Formula (7) represents a (Z)-2-methyl-2,6-heptadiene compound of the following formula (7a) having a protected hydroxyl group at position 1 or an (E)-2-methyl-2,6-heptadiene compound of the following formula (7b) having a protected hydroxyl group at position 1, or a combination thereof.

(7a)

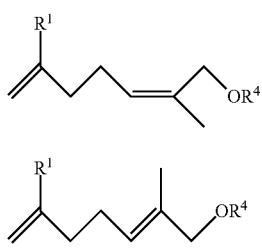

(7b)

Step A'

The 2-methyl-2,6-heptadiene compound (7) having a protected hydroxyl group at position 1 is thought to be synthesized by carrying out a Wittig reaction between the 4-pentenyltriphenylphosphonium halide compound (5) and the 2-propanone compound (6) having a protected hydroxyl group.

In consideration of the retrosynthetic analysis mentioned above, an embodiment of the present invention may be depicted by the following chemical reaction scheme. Steps A to F shown below correspond to steps A' to F' in the reaction formulae of the retrosynthetic analysis shown above, respectively.

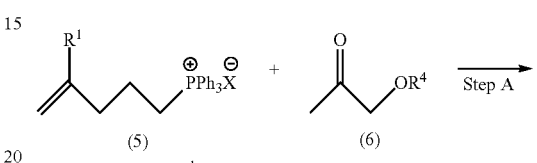

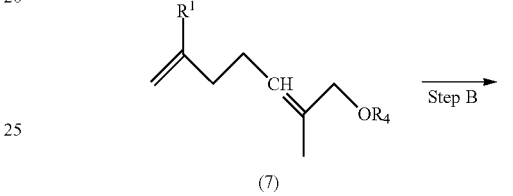

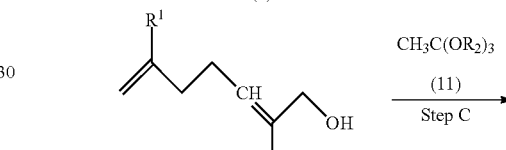

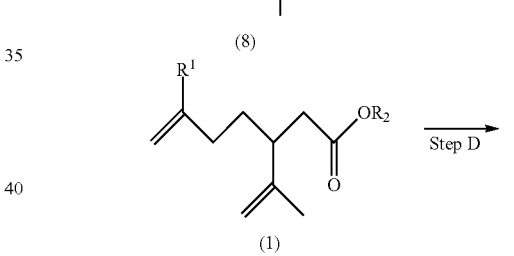

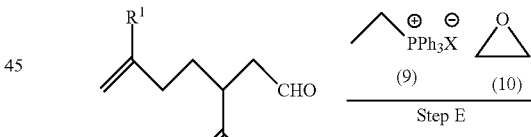

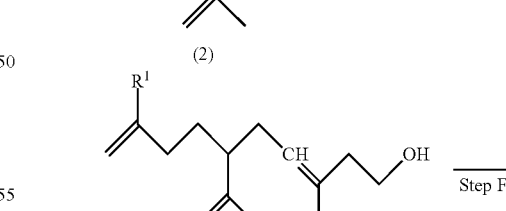

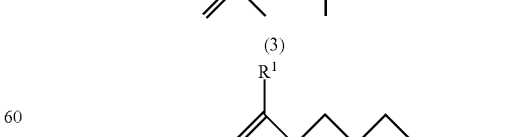

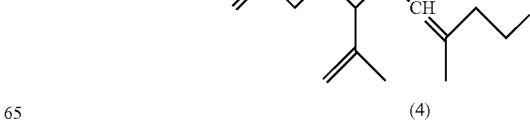

Thus, the synthesis of the 3-isopropenyl-6-heptenal compound (2) may be synthesized by selectively reducing an ester group of the 3-isopropenyl-6-heptenoate ester compound (1) to an aldehyde group (step D), whereby a 6-isopropenyl-3-methyl-3,9-decadienol compound (3) (step E) and a 6-isopropenyl-3-methyl-3,9-decadienyl carboxylate compound (4) (step F) may be easily obtained.

Steps A to F, which are embodiments of the present invention, will be described below in detail. These will be explained in the order of steps D, E, F, A, B, and C.

Steps D to F and, then, steps A to C, which are embodiments of the present invention, will be described below in detail.

[1] Step D

Step D to synthesize a 3-isopropenyl-6-heptenal compound (2) will be described below. The 3-isopropenyl-6-heptenal compound (2) is obtained, for example, by subjecting a 3-isopropenyl-6-heptenoate ester compound (1) obtained in step C as detailed below to a reduction reaction with a reducing agent to reduce the ester group of the 3-isopropenyl-6-heptenoate ester compound (1), as shown in the following chemical reaction formula.

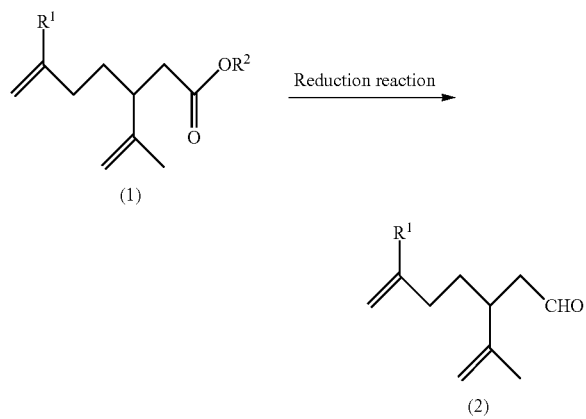

First, the 3-isopropenyl-6-heptenoate ester compound of the following formula (1) will be described.

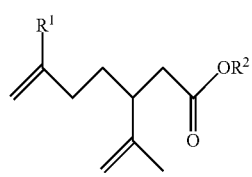

The 3-isopropenyl-6-heptenoate ester compound (1) may be an (R)-3-isopropenyl-6-heptenoate ester compound of the following formula (1a) or an (S)-3-isopropenyl-6-heptenoate ester compound of the following formula (1b). The 3-isopropenyl-6-heptenoate ester compound (1) may be either a single isomer or a combination of the isomers, but preferably contains the compound (1a) having the same backbone as a naturally occurring sex pheromone borne by female California red scale and White peach scale.

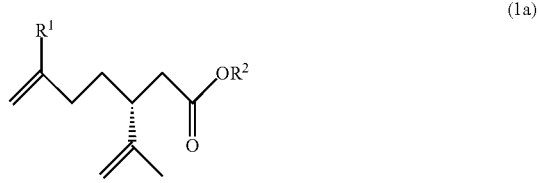

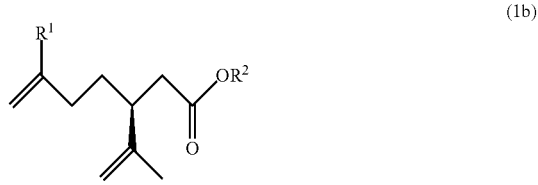

$R^1$ represents a hydrogen atom or a methyl group, and $R^2$ represents a monovalent hydrocarbon group having 1 to 10, preferably 1 to 5, carbon atoms.

Examples of the monovalent hydrocarbon group include linear or branched saturated hydrocarbon groups such as a methyl group, an ethyl group, an n-propyl group, an n-butyl group, an n-pentyl group, and a 1-methylethyl group; linear or branched unsaturated hydrocarbon groups such as a vinyl group, a 1-propenyl group, a 2-propenyl group, a 2-methyl-1-propenyl group, an ethinyl group, a propynyl group, and a 1-butynyl group; and isomers thereof. Apart of the hydrogen atoms in the monovalent hydrocarbon groups may be substituted with a methyl group or an ethyl group.

The monovalent hydrocarbon group may be appropriately selected in view of the reactivity in a subsequent reaction and/or the availability.

Specific examples of the 3-isopropenyl-6-heptenoate ester compound (1) include 3-isopropenyl-6-heptenoate ester compounds such as methyl 3-isopropenyl-6-heptenoate, ethyl 3-isopropenyl-6-heptenoate, and propyl 3-isopropenyl-6-heptenoate; and 3-isopropenyl-6-methyl-6-heptenoate ester compounds (1') such as methyl 3-isopropenyl-6-methyl-6-heptenoate, ethyl 3-isopropenyl-6-methyl-6-heptenoate, and propyl 3-isopropenyl-6-methyl-6-heptenoate.

Among the 3-isopropenyl-6-heptenoate ester compound (1), a 3-isopropenyl-6-methyl-6-heptenoate ester compound (1') shown below, wherein $R^1$ in formula (1) is a methyl group, is useful in view of the availability as an intermediate used in the preparation of the sex pheromone of female White peach scale.

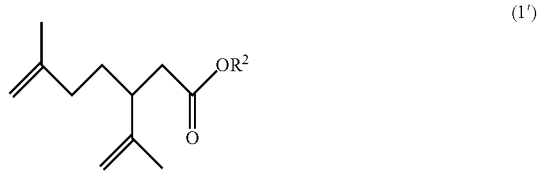

$R^2$ is as defined for the formula (1).

Next, a 3-isopropenyl-6-heptenal compound of the following formula (2) will be described.

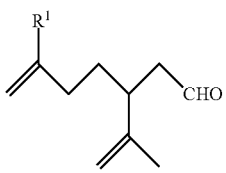

(2)

The 3-isopropenyl-6-heptenal compound (2) may be an (R)-3-isopropenyl-6-heptenal compound of the following formula (2a) or an (S)-3-isopropenyl-6-heptenal compound of the following formula (2b). The 3-isopropenyl-6-heptenal compound (2) may be either a single isomer or a combination of the isomers, but preferably contains the compound (2a) having the same backbone as a naturally occurring sex pheromone borne by female California red scale and White peach scale.

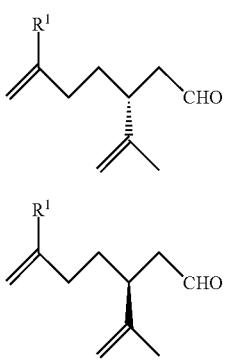

(2a)

(2b)

$R^1$ is as defined for the formula (1).

Specific examples of the 3-isopropenyl-6-heptenal compound (2) include 3-isopropenyl-6-heptenal and 3-isopropenyl-6-methyl-6-heptenal.

The 3-isopropenyl-6-heptenal compound (2) may be synthesized by selectively reducing an ester group of the 3-isopropenyl-6-heptenoate ester compound (1) into an aldehyde group. The reduction reaction of the ester group may be carried out using a reducing agent in the presence or absence of a solvent, if necessary, with heating or cooling.

When over-reduction occurs in the reduction reaction of the ester group, an alcohol may be by-produced. Optimal conditions may be adopted, among the reduction conditions described below, to reduce the by-production of an alcohol from over-reduction and to enhance selectivity for the 3-isopropenyl-6-heptenal compound (2). Examples of the optimal conditions include sodium diisobutyl t-butoxy aluminum hydride, as a reducing agent, prepared from sodium t-butoxide and aluminum diisobutyl hydride in situ in a reaction system, tetrahydrofuran as a solvent, and a reaction temperature of 10° C. or lower; or combinations thereof.

Examples of the reducing agent used in the reduction reaction include hydrogen; boron compounds such as borane, alkylborane, and dialkylborane; metal hydrides such as dialkylsilane, estersilane, alkylaluminum, dialkylaluminum, sodium hydride, lithium hydride, potassium hydride, and calcium hydride; complex hydrides such as sodium borohydride, lithium borohydride, potassium borohydride, calcium borohydride, sodium aluminum hydride, sodium diisobutylalkoxy aluminum hydride, potassium diisobutylalkoxy aluminum hydride, lithium diisobutylalkoxy aluminum hydride, lithium aluminum hydride, sodium trimethoxy borohydride, lithium trimethoxy aluminum hydride, lithium diethoxy aluminum hydride, lithium tri-t-butoxy aluminum hydride, sodium bis(2-methoxyethoxy) aluminum hydride, lithium triethyl borohydride, aluminum diisobutyl hydride, and diisobutylalkoxy hydride; and alkoxy derivatives or alkyl derivatives of the complex hydrides. Aluminum diisobutyl hydride, sodium diisobutylalkoxy aluminum hydride, potassium diisobutylalkoxy aluminum hydride, and lithium diisobutylalkoxy aluminum hydride are preferred in view of reaction conditions and/or easy post-treatments and/or-easy product isolation. Preferably, sodium diisobutylalkoxy aluminum hydride, potassium diisobutylalkoxy aluminum hydride, and lithium diisobutylalkoxy aluminum hydride are prepared in situ in a reaction system. These may be prepared, for example, by mixing aluminum diisobutyl hydride and its corresponding alkoxy metal salt in any ratio. Particularly preferred examples of the reducing agent that suppresses over-reduction into an alcohol so as to enhances a yield for an aldehyde include sodium diisobutyl t-butoxy aluminum hydride, potassium diisobutyl t-butoxy aluminum hydride, and lithium diisobutyl t-butoxy aluminum hydride.

An amount of the reducing agent used in the reduction reaction varies, depending on a species of the reducing agent and/or reaction conditions, and is preferably from 0.5 mol to 1000000 mol, more preferably from 0.9 to 200 mol, per mol of the 3-isopropenyl-6-heptenoate ester compound (1).

A solvent used in the reduction reaction varies, depending on a species of the reducing agent. Preferred examples of the solvent include water; hydrocarbons such as hexane, heptane, benzene, toluene, xylene, and cumene; ethers such as diethyl ether, dibutyl ether, diethylene glycol diethyl ether, diethylene glycol dimethyl ether, tetrahydrofuran, and 1,4-dioxane; alcohols such as methanol, ethanol, 1-propanol, 2-propanol, ethylene glycol monomethyl ether, and diethylene glycol monomethyl ether; nitriles such as acetonitrile; and aprotic polar solvents such as N,N-dimethylformamide, dimethyl sulfoxide, and hexamethylphosphoric triamide.

The solvent may be used alone or in combination thereof, if necessary. The solvent may be commercially available one.

An amount of the solvent used is preferably from 10 g to 10,000 g, per mol of the 3-isopropenyl-6-heptenoate ester compound (1).

A reaction temperature of the reduction is preferably from −78° C. to a boiling point of the solvent, more preferably from −78° C. to 50° C.

A reaction time of the reduction may be arbitrarily set. In view of the yield, it is desirable to monitor progress of the reaction with gas chromatography (GC) and/or thin layer chromatography (TLC) to complete the reaction. The reaction time is typically from about 0.5 to 72 hours.

When the 3-isopropenyl-6-heptenal compound (2) thus obtained has a sufficient purity, it may be used as such in a subsequent step. Alternatively, a crude product may be purified in any purification method used in usual organic synthesis, such as distillation or various chromatography. Distillation is particularly preferred in view of the industrial economy.

[2] Step E

Step E to synthesize a 6-isopropenyl-3-methyl-3,9-decadienol compound (3) will be described below. The 6-isopropenyl-3-methyl-3,9-decadienol compound (3) may be obtained by subjecting the 3-isopropenyl-6-heptenal compound (2) obtained step D to four-carbon homologation including a Wittig reaction, using an ethyltriphenylphosphonium halide compound (9) and ethylene oxide (10), as shown in the following reaction formula.

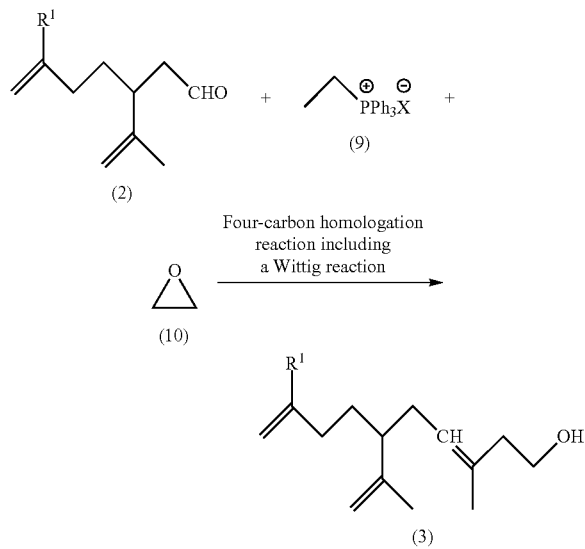

First, the ethyltriphenylphosphonium halide compound of the following formula (9) will be described.

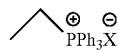

(9)

In the formula, X represents a halogen atom, preferably a chlorine atom, a bromine atom, or an iodine atom.

The ethyltriphenylphosphonium halide compound (9) may be commercially available one.

Alternatively, the ethyltriphenylphosphonium halide compound (9) may be prepared by reacting an ethyl halide compound of the following formula (12) with triphenylphosphine (PPh$_3$) in a solvent, according to the following reaction formula.

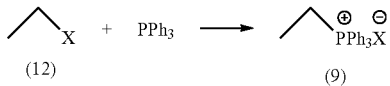

X in the formula (12) is as defined for the formula (9).

In the preparation of the ethyltriphenylphosphonium halide compound (9), a metal halide and/or a quaternary onium salt may be added to accelerate the reaction. Examples of the metal halide include lithium iodide, sodium iodide, potassium iodide, lithium bromide, sodium bromide, and potassium bromide. Examples of the quaternary onium salt include tetraethylammonium bromide, tetrabutylammonium bromide, tetrabutylphosphonium bromide, tetraethylammonium iodide, tetrabutylammonium iodide, and tetrabutylphosphonium iodide.

In the preparation of the ethyltriphenylphosphonium halide compound (9), the reaction mixture may be made basic by adding one or more bases selected from bicarbonates such as lithium bicarbonate, sodium bicarbonate, and potassium bicarbonate; carbonates such as lithium carbonate, sodium carbonate, and potassium carbonate; hydroxide salts such as lithium hydroxide, sodium hydroxide, and potassium hydroxide; and organic bases such as triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine, and morpholine.

The solvent used in the preparation of the ethyltriphenylphosphonium halide compound (9) may be those as will be described for a Wittig reaction.

An amount of the solvent is preferably from 10 g to 10,000 g, per mol of the ethyl halide compound (12).

A reaction temperature of the preparation of the ethyltriphenylphosphonium halide compound (9) varies, depending on reaction conditions, and may be from −10° C. to 180° C., preferably from 0° C. to 160° C., and more preferably from 10° C. to 140° C.

A reaction time of the preparation of the ethyltriphenylphosphonium halide compound (9) may be arbitrarily set. In view of the yield, it is desirable to monitor progress of the reaction with gas chromatography (GC) and/or thin layer chromatography (TLC) to complete the reaction. The reaction time is typically from about 0.5 to 60 hours.

Next, the 6-isopropenyl-3-methyl-3,9-decadienol compound of the following formula (3) will be described.

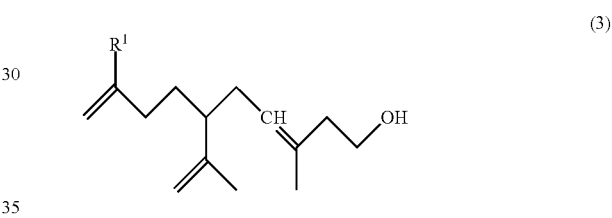

The 6-isopropenyl-3-methyl-3,9-decadienol compound (3) may be a (3Z,6R)-6-isopropenyl-3-methyl-3,9-decadienol compound of the following formula (3a), a (3E,6R)-6-isopropenyl-3-methyl-3,9-decadienol compound of the following formula (3b), a (3Z,6S)-6-isopropenyl-3-methyl-3,9-decadienol compound of the following formula (3c), or a (3E,6S)-6-isopropenyl-3-methyl-3,9-decadienol compound of the following formula (3d). The 6-isopropenyl-3-methyl-3,9-decadienol compound (3) may be either a single isomer or a combination of the isomers, but preferably comprises the compound (3a) having the same backbone as a naturally occurring sex pheromone borne by female California red scale and White peach scale.

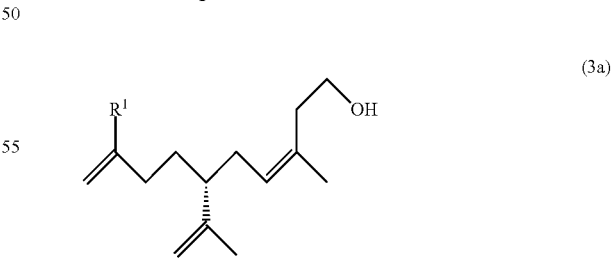

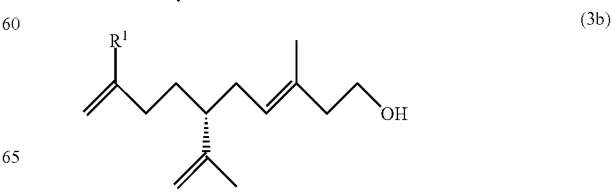

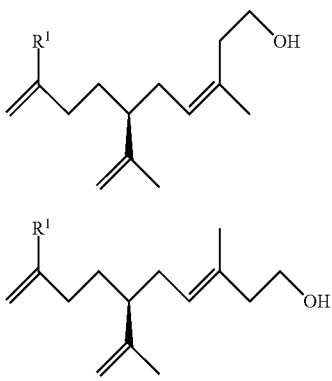

Here, $R^1$ is as defined for the formula (1).

The Wittig reaction refers to a chemical reaction to synthesize an alkene from a carbonyl compound using phosphorus ylide called a Wittig reagent.

The four-carbon homologation including a Wittig reaction will be described below, by way of example, for a compound wherein $R^1$ represents a hydrogen atom. Then, in a case where $R^1$ represents $CH_3$, the number of the carbon atoms in the units having $R^1$ is larger by one.

The four-carbon homologation including a Wittig reaction may take either of the two routes, Reaction Route 1 and Reaction Route 2 described below.

In Reaction Route 1, an ethyltriphenylphosphonium halide compound (9) having two carbon atoms (C2) is reacted with a base to form an ylide (13). This ylide (13) is reacted with ethylene oxide (10) having two carbon atoms (C2) to form 3-triphenylphosphoniobutoxide (14) having a four-carbon backbone (C4) (C2+C2=C4). Then, 3-triphenylphosphoniobutoxide (14) thus obtained is reacted with a base to form phosphorus ylide (15). This phosphorus ylide (15) is subjected to a Wittig reaction with a 3-isopropenyl-6-heptenal compound (2) having ten carbon atoms (C10) to form a 6-isopropenyl-3-methyl-3,9-decadienol compound (3) having 14 carbon atoms (C14) (C4+C10=C14).

In Reaction Route 2, an ethyltriphenylphosphonium halide compound (9) having two carbon atoms (C2) is reacted with a base to form an ylide (13). This ylide (13) is reacted with a 3-isopropenyl-6-heptenal compound (2) having ten carbon atoms (C10) to form an intermediate, betaine (16) having a 12-carbon backbone (C12) (C2+C10=C12). The intermediate, betaine (16), is reacted with a base to form β-oxidophosphorus ylide (17). Then, β-oxidophosphorus ylide (17) thus obtained is reacted with ethylene oxide (10) having two carbon atoms (C2) to form a 6-isopropenyl-3-methyl-3,9-decadienol compound (3) having 14 carbon atoms (C14) (C12+C2=C14).

The synthesis method of Reaction Route 2 is generally known as three-dimensional Wittig reaction or α-Substitution plus Carbonyl Olefination via β-Oxido Phosphorous Ylides (SCOOPY) reaction (see, for example, Non-Patent Literature 4 listed above).

Among these Reaction Routes, a more industrially suitable process might be adopted in view of the economy, reactivity, and yield. Reaction Route 1 is preferred in view of the yield.

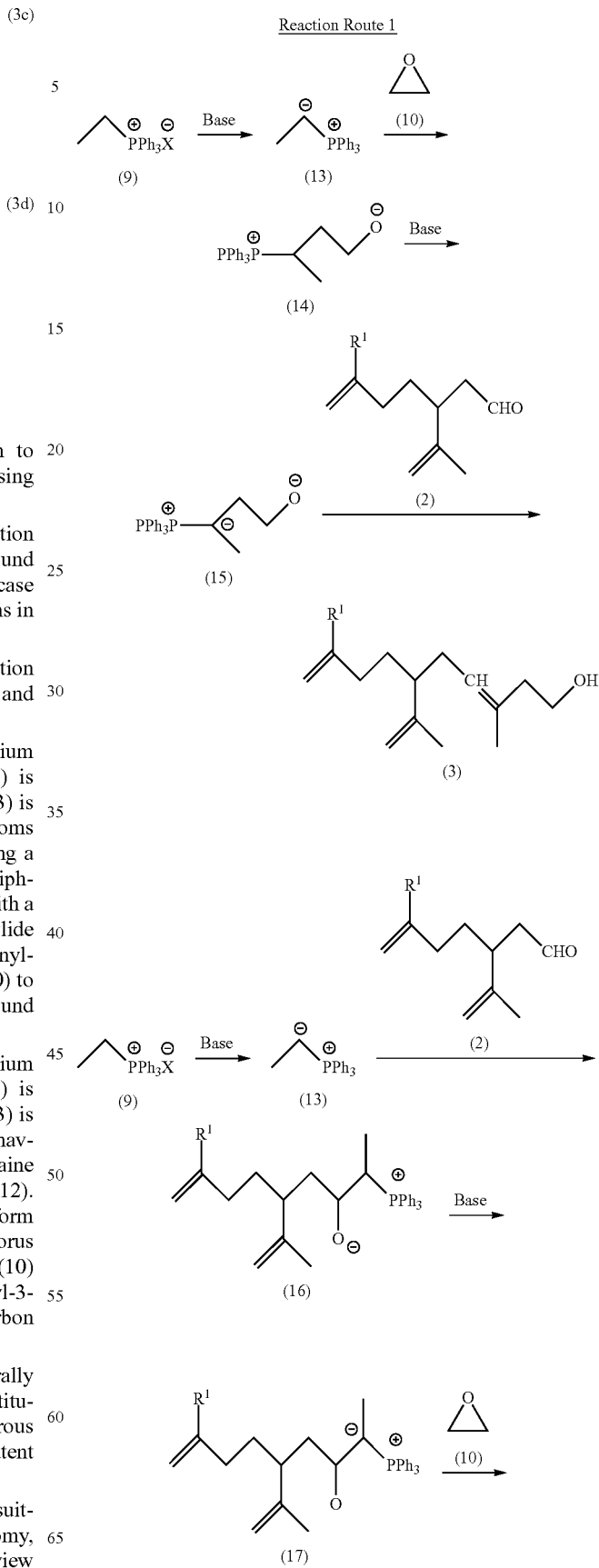

Reaction Route 1

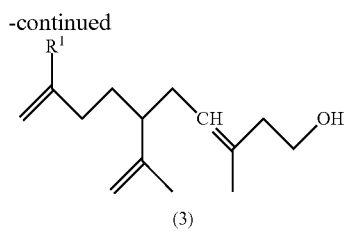

(3)

First, Reaction Route 1 will be described below in detail.

The preparation of ylide (13) from an ethyltriphenylphosphonium halide compound (9) having two carbon atoms (C2) may be carried out by adding a base to the ethyltriphenylphosphonium halide compound (9) in a solvent, if necessary, with heating or cooling.

Examples of the base used in the preparation of ylide (13) include metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide; organometallic reagents such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; and metal hydrides such as sodium hydride, potassium hydride, and calcium hydride.

The base may be used either alone or in combination thereof, and is chosen, depending upon compound (9), and/or reactivity and/or selectivity.

An amount of the base is preferably from 0.7 mol to 5 mol, per mol of the ethyltriphenylphosphonium halide compound (9).

The solvent used in the preparation of ylide (13) may be same as that used in the Wittig reaction, as described below.

An amount of the solvent is preferably from 10 g to 10,000 g, per mol of the ethyltriphenylphosphonium halide compound (9).

A reaction temperature of the preparation of ylide (13) is preferably from −78 to 50° C., more preferably from −78° C. to 35° C.

A reaction time of the preparation of ylide (13) is preferably from 5 minutes to 18 hours, more preferably from 5 minutes to 10 hours, in view of the stability of the reactants.

Next, ylide (13) is reacted with ethylene oxide (10) having two carbon atoms (C2) in a solvent to increase the number of carbon atoms by two so as to form 3-triphenylphosphoniobutoxide (14) having a four-carbon backbone (C4).

An amount of ethylene oxide (10) used in the two-carbon homologation is preferably from 0.6 mol to 5 mol, per mol of the ethyltriphenylphosphonium halide compound (9).

A solvent in the two-carbon homologation may be same as that used in the Wittig reaction, as described below.

An amount of the solvent is preferably from 10 g to 10,000 g, per mol of the ethyltriphenylphosphonium halide compound (9).

A reaction temperature of the two-carbon homologation is preferably from −78 to 50° C., more preferably −78° C. to 35° C.

A reaction time of the two-carbon homologation is preferably from 5 minutes to 18 hours, more preferably from 5 minutes to 10 hours in view of the stability of the reactants.

Next, 3-triphenylphosphoniobutoxide (14) obtained in the two-carbon homologation is reacted with a base in a solvent, if necessary, with heating or cooling to form phosphorus ylide (15).

The base, an amount of the base, a solvent, a reaction temperature, and a reaction time in the preparation of phosphorus ylide (15) from 3-triphenylphosphoniobutoxide (14) may be same as those mentioned for the preparation of ylide (13).

Finally, phosphorus ylide (15) is subjected to a Wittig reaction with a 3-isopropenyl-6-heptenal compound (2) having ten carbon atoms (C10), if necessary, with cooling or heating to form a 6-isopropenyl-3-methyl-3,9-decadienol compound (3) having 14 carbon atoms (C14).

An amount of the 3-isopropenyl-6-heptenal compound (2) used in the Wittig reaction is preferably from 0.1 mol to 5 mol, per mol of the ethyltriphenylphosphonium halide compound (9).

Examples of the solvent used in the Wittig reaction include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

An amount of the solvent is preferably from 10 g to 10,000 g, per mol of the ethyltriphenylphosphonium halide compound (9).

A reaction temperature of the Wittig reaction is preferably from −78° C. to 50° C., more preferably from −50° C. to 35° C.

A reaction time of the Wittig reaction may be arbitrarily set. In view of the yield, it is desirable to monitor progress of the reaction with gas chromatography (GC) and/or thin layer chromatography (TLC) to complete the reaction. The reaction time is typically from about 0.5 to 24 hours.

Next, Reaction Route 2 will be described below in detail.

The preparation of ylide (13) from an ethyltriphenylphosphonium halide compound (9) having two carbon atoms (C2) may be carried out by adding a base to the ethyltriphenylphosphonium halide compound (9) in a solvent, if necessary, with heating or cooling. The base, an amount of the base, a solvent, a reaction temperature, and a reaction time in this process for preparing ylide (13) may be same as those mentioned for the preparation of ylide (13) described above.

Next, ylide (13) is reacted with a 3-isopropenyl-6-heptenal compound (2) having ten carbon atoms (C10) in a solvent to increase the number of carbon atoms by ten so as form an intermediate, betaine (16) having a 12-carbon backbone (C12).

An amount of the 3-isopropenyl-6-heptenal compound (2) used in the preparation of the intermediate, betaine, is preferably from 0.1 mol to 5 mol, per mol of the ethyltriphenylphosphonium halide compound (9).

Examples of the solvent used in the preparation of the intermediate, betaine, include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

An amount of the solvent is preferably from 10 g to 10,000 g, per mol of the ethyltriphenylphosphonium halide compound (9).

A reaction temperature of the preparation of the intermediate, betaine, is preferably from −78° C. to 50° C., more preferably from −78° C. to 20° C.

A reaction time of the preparation of the intermediate, betaine, may be arbitrarily set, and is usually from about 0.001 to 24 hours.

Next, the prepared intermediate, betaine (16), is reacted with a base to form β-oxidophosphorus ylide (17).

The base, an amount of the base, a solvent, a reaction temperature, and a reaction time in the preparation of β-oxide phosphorus ylide (17) may be same as those mentioned for the preparation of ylide (13).

Finally, β-oxidophosphorus ylide (17) is subjected to a two-carbon homologation with ethylene oxide (10) in a solvent to form a 6-isopropenyl-3-methyl-3,9-decadienol compound (3) having 14 carbon atoms (C14).

An amount of ethylene oxide (10), a solvent, a reaction temperature, and a reaction time may be same as those mentioned for the preparation of 3-triphenylphosphoniobutoxide (14).

When the 6-isopropenyl-3-methyl-3,9-decadienol compound (3) obtained in the step has a sufficient purity, it may be used as such in a subsequent step. Alternatively, the crude product may be purified in any purification method used in usual organic synthesis, such as distillation or various chromatography. Distillation is particularly preferred in view of the industrial economy.

[3] Step F

Step F to synthesize a 6-isopropenyl-3-methyl-3,9-decadienyl carboxylate compound (4) will be described below. The 6-isopropenyl-3-methyl-3,9-decadienyl carboxylate compound (4) may be obtained by subjecting the 6-isopropenyl-3-methyl-3,9-decadienol compound (3) obtained in step E to an esterification reaction, as shown in the following reaction formula.

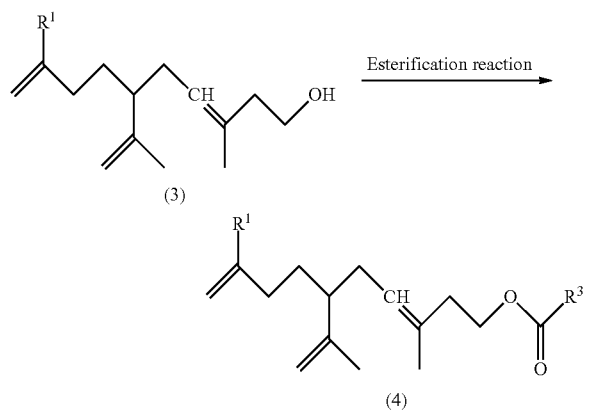

The 6-isopropenyl-3-methyl-3,9-decadienyl carboxylate compound of the following formula (4) will be explained below.

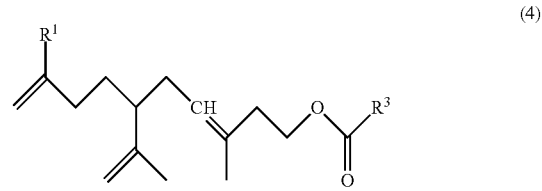

The 6-isopropenyl-3-methyl-3,9-decadienyl carboxylate compound (4) may be a (3Z,6R)-6-isopropenyl-3-methyl-3,9-decadienyl carboxylate compound of the following formula (4a), a (3E,6R)-6-isopropenyl-3-methyl-3,9-decadienyl carboxylate compound of the following formula (4b), a (3Z,6S)-6-isopropenyl-3-methyl-3,9-decadienyl carboxylate compound of the following formula (4c), or a (3E,6S)-6-isopropenyl-3-methyl-3,9-decadienyl carboxylate compound of the following formula (4d). The 6-isopropenyl-3-methyl-3,9-decadienyl carboxylate compound (4) may be either a single isomer or a combination of the isomers, but preferably contains the compound (4a) having the same backbone as a naturally occurring sex pheromone borne by female California red scale and White peach scale.

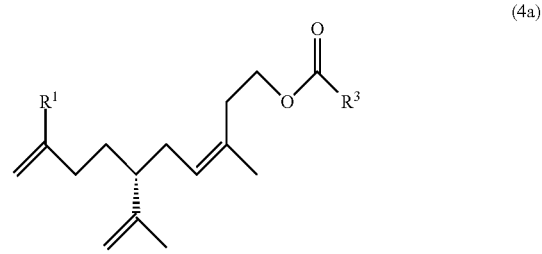

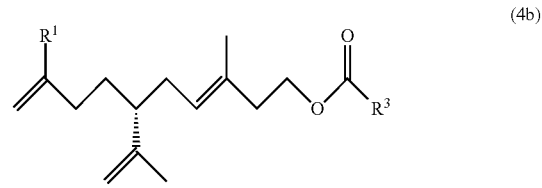

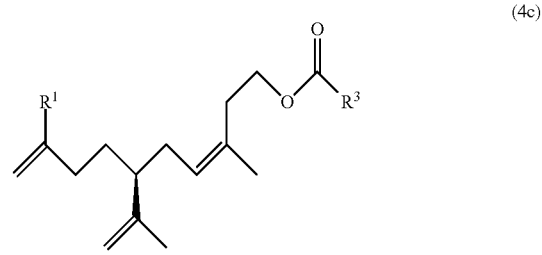

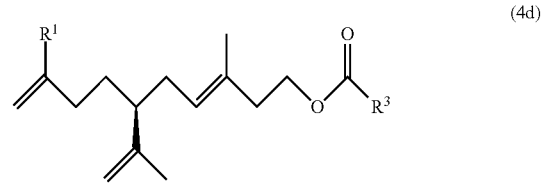

Here, $R^1$ is as defined for the formula (1). $R^3$ represents a hydrogen atom or a monovalent hydrocarbon group having 1 to 10, preferably 1 to 5 carbon atoms. Examples of the monovalent hydrocarbon group include linear or branched saturated hydrocarbon groups such as a methyl group, an ethyl group, an n-propyl group, an n-butyl group, an n-pentyl group, and a 1-methylethyl group; linear or branched unsaturated hydrocarbon groups such as a vinyl group, a 1-propenyl group, a 2-propenyl group, a 2-methyl-1-propenyl group, an ethinyl group, a propynyl group, and a 1-butynyl group; and isomers thereof. Apart of the hydrogen atoms in the monovalent hydrocarbon groups may be substituted with a methyl group or an ethyl group.

The monovalent hydrocarbon group used in the reaction may be appropriately selected from these in view of the reactivity in a subsequent reaction and/or the availability.

Specific examples of the 6-isopropenyl-3-methyl-3,9-decadienyl carboxylate compound (4) include 6-isopropenyl-3-methyl-3,9-decadienyl acetate, 6-isopropenyl-3-methyl-3,9-decadienyl propionate, 6-isopropenyl-3,9-dimethyl-3,9-decadienyl acetate, and 6-isopropenyl-3,9-dimethyl-3,9-decadienyl propionate.

The esterification reaction may be carried out in any known ester formation method, for example, (i) a reaction with an acylating agent, (ii) a reaction with a carboxylic acid, (iii) a transesterification, and (iv) a reaction of converting a hydroxyl group of a 6-isopropenyl-3-methyl-3,9-decadienol compound (3) into a leaving group and then reacting with a carboxylic acid.

(i) Reaction with an Acylating Agent

The reaction with an acylating agent may be carried out by reacting a 6-isopropenyl-3-methyl-3,9-decadienol compound (3) with an acylating agent and a base in this order, in the reversed order, or simultaneously, in a single solvent or a mixed solvent.

Examples of the acylating agent include acyl halides such as acyl chloride and acyl bromide; carboxylic anhydride, and mixed carboxylic anhydrides such as mixed carboxylic/trifluoroacetic anhydride, mixed carboxylic/methanesulfonic anhydride, mixed carboxylic/trifluoromethanesulfonic anhydride, mixed carboxylic/benzensulfonic anhydride and mixed carboxylic/p-toluenesulfonic anhydride; and p-nitrophenyl carboxylate.

Specific examples of the acyl chloride include acetyl chloride, propionyl chloride, crotonoyl chloride, and benzoyl chloride. Examples of the carboxylic anhydride include acetic anhydride and propionic anhydride.

An amount of the acylating agent used is preferably from 1 to 500 mol, more preferably from 1 to 50 mol, and even more preferably from 1 to 5 mol, per mol of the 6-isopropenyl-3-methyl-3,9-decadienol compound (3).

Examples of the base used in the reaction with the acylating agent include N,N-diisopropylethylamine, N,N-dimethylaniline, N,N-diethylaniline, pyridine, 2-ethylpyridine, and 4-dimethylaminopyridine.

An amount of the base used is from 1 to 500 mol, per mol of the 6-isopropenyl-3-methyl-3,9-decadienol compound (3).

The solvent used in the reaction with the acylating agent may be the base described above. Examples of the solvent include chlorinated solvents such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide.

The solvent may be used alone or in combination thereof, if necessary. The solvent may be commercially available one.

An amount of the solvent used is preferably from 10 to 1,000,000 g, per mol of the 6-isopropenyl-3-methyl-3,9-decadienol compound (3).

The reaction with the acylating agent such as a carboxylic anhydride, a mixed carboxylic anhydride, and p-nitrophenyl carboxylate may be carried out in the presence of an acid catalyst instead of the base.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium (IV) oxide.

The acid catalyst may be used alone or in combination thereof, if necessary. The acid catalyst may be commercially available one.

An amount of the acid catalyst used in the reaction with the acylating agent such as carboxylic anhydride, mixed carboxylic anhydride, or p-nitrophenyl carboxylate is preferably from 0.0001 to 100 mol.

A reaction temperature of the reaction with the acylating agent may be appropriately selected, depending on a type of the acylating agent and/or reaction conditions. Typically, the reaction temperature is preferably from −50° C. to a boiling point of the solvent, more preferably from −20° C. to room temperature (5° C. to 35° C., hereinafter the same).

A reaction time of the reaction with the acylating agent may be arbitrarily set and may be optimized by monitoring the reaction progress with gas chromatography (GC) or thin layer chromatography (TLC). The reaction time is typically and preferably from 5 minutes to 240 hours.

(ii) Reaction with a Carboxylic Acid

The reaction with a carboxylic acid is a dehydration reaction between the 6-isopropenyl-3-methyl-3,9-decadienol compound (3) and a carboxylic acid and is carried out typically in the presence of an acid catalyst.

Specific examples of the carboxylic acid used in the reaction between the 6-isopropenyl-3-methyl-3,9-decadienol compound (3) and a carboxylic acid include linear saturated carboxylic acids such as formic acid, acetic acid, propionic acid, butyric acid, valeric acid, and caproic acid; branched saturated carboxylic acids such as isobutyric acid, isovaleric acid, 4-methylpentanoic acid, 2-methylbutanoic acid, and pivalic acid; linear unsaturated carboxylic acids such as acrylic acid, crotonic acid, and 3-butenoic acid; branched unsaturated carboxylic acids such as methacrylic acid, senecioic acid, tiglic acid, angelic acid, 3-methyl-4-pentenoic acid, and 4-methyl-4-pentenoic acid; and aromatic carboxylic acids such as benzoic acid.

An amount of the carboxylic acid used is preferably from 1 to 500 mol, more preferably from 1 to 50 mol, and even more preferably from 1 to 5 mol, per mol of the 6-isopropenyl-3-methyl-3,9-decadienol compound (3).

An acid catalyst may be used in the reaction between the 6-isopropenyl-3-methyl-3,9-decadienol compound (3) and the carboxylic acid. The acid catalyst may be same as that used in the reaction with the acylating agent.

An amount of the acid catalyst used is preferably from 0.0001 to 100 mol, more preferably from 0.001 to 1 mol, and even more preferably from 0.01 to 0.05 mol, per mol of the 6-isopropenyl-3-methyl-3,9-decadienol compound (3).

A solvent and an amount of the solvent used in the reaction between the 6-isopropenyl-3-methyl-3,9-decadienol compound (3) and the carboxylic acid may be same as those used in the reaction with the acylating agent.

A reaction temperature of the reaction between the 6-isopropenyl-3-methyl-3,9-decadienol compound (3) and the carboxylic acid may be appropriately selected, depending on reaction conditions. Typically, the reaction temperature is preferably from −50° C. to a boiling point of the solvent, more preferably from room temperature to a boiling point of the solvent.

The reaction may be done in a solvent such as hydrocarbons such as hexane, heptane, benzene, toluene, xylene, and cumene, while removing formed water from the reaction system by azeotropic distillation. Alternatively, water may be distilled off with refluxing at a boiling point of the solvent at normal pressure, or at a lower temperature than a boiling point of the solvent at a reduced pressure.

A reaction time of the reaction with the carboxylic acid may be arbitrarily set and may be optimized by monitoring the reaction progress with gas chromatography (GC) or thin layer chromatography (TLC). The reaction time is typically and preferably from 5 minutes to 240 hours.

(iii) Transesterification

The transesterification is carried out by reacting the 6-isopropenyl-3-methyl-3,9-decadienol compound (3) with an alkyl carboxylate in the presence of a catalyst, while removing a formed alcohol.

The alkyl carboxylate is preferably a primary alkyl ester of a carboxylic acid. Methyl carboxylate, ethyl carboxylate, and n-propyl carboxylate are preferred in view of the price and/or easier progress of the reaction.

Examples of the carboxylic acid may be those for the esterification reaction with a carboxylic acid.

An amount of the alkyl carboxylate used is preferably from 1 to 500 mol, more preferably from 1 to 50 mol, and even more preferably from 1 to 5 mol, per mol of the 6-isopropenyl-3-methyl-3,9-decadienol compound (3).

Examples of the catalyst used in the transesterification include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The catalyst may be used alone or in combination thereof, if necessary. The catalyst may be commercially available one.

An amount of the catalyst used is preferably from 0.0001 to 100 mol, more preferably from 0.001 to 1 mol, and even more preferably from 0.01 to 0.05 mol, per mol of the 6-isopropenyl-3-methyl-3,9-decadienol compound (3).

The transesterification may be carried out without a solvent wherein the alkyl carboxylate works as a solvent, or with a solvent. It is preferred not to use a solvent, so that any extra operation, such as concentration or solvent recovery, is unnecessary.

Examples of the solvent used in the transesterification include hydrocarbons such as hexane, heptane, benzene, toluene, xylene, and cumene; and ethers such as diethyl ether, dibutyl ether, diethylene glycol diethyl ether, diethylene glycol dimethyl ether, tetrahydrofuran, and 1,4-dioxane.

The solvent may be used alone or in combination thereof, if necessary. The solvent may be commercially available one.

An amount of the solvent used is preferably from 10 to 1,000,000 g, per mol of the 6-isopropenyl-3-methyl-3,9-decadienol compound (3).

A reaction temperature of the transesterification may be appropriately selected, depending on a species of the alkyl carboxylate and/or reaction conditions. The transesterification is typically carried out with heating. In view of easier progress of reaction, the transesterification is preferably carried out around a boiling point of a lower $C_{1-3}$ alcohol which generates in the transesterification, such as methanol, ethanol, or 1-propanol, while distilling off the formed lower alcohol. The alcohol may be distilled off at a lower temperature than its boiling point at a reduced pressure.

A reaction time of the transesterification may be arbitrarily set and may be optimized by monitoring the reaction progress with gas chromatography (GC) or thin layer chromatography (TLC). The reaction time is typically and preferably from 5 minutes to 240 hours.

(iv) Reaction of Converting a Hydroxyl Group of a 6-isopropenyl-3-methyl-3,9-decadienol Compound (3) into a Leaving Group and then Reacting with a Carboxylic Acid The reaction of converting a hydroxyl group of the 6-isopropenyl-3-methyl-3,9-decadienol compound (3) into a leaving group may be carried out by, for example, converting a hydroxyl group of the 6-isopropenyl-3-methyl-3,9-decadienol compound (3) into a leaving group selected from a halogen atom such as a chlorine atom, a bromine atom, or an iodine atom; an alkanesulfonyloxy group such as a methanesulfonyloxy group or a trifluoromethanesulfonyloxy group; and an arenesulfonyloxy group such as a benzenesulfonyloxy group or a p-toluenesulfonyloxy group, and then reacting the formed compound with a carboxylic acid in a solvent in the presence of a base.

Examples of the carboxylic acid may be those for the reaction with a carboxylic acid.

An amount of the carboxylic acid used is preferably from 1 to 500 mol, more preferably from 1 to 50 mol, and even more preferably from 1 to 5 mol, per mol of the 6-isopropenyl-3-methyl-3,9-decadienol compound (3).

The solvent, an amount of the solvent, the base, an amount of the base, a reaction time, and a reaction temperature in the reaction of converting a hydroxyl group of the 6-isopropenyl-3-methyl-3,9-decadienol compound (3) into a leaving group may be same as those mentioned for the reaction between the 6-isopropenyl-3-methyl-3,9-decadienol compound (3) and an acylating agent ((i) Reaction with an acylating agent).

A carboxylate salt such as sodium carboxylate, lithium carboxylate, potassium carboxylate, or ammonium carboxylate may be used instead of the combination of the carboxylic acid with the base. An amount of the carboxylate salt is same as the amount of the carboxylic acid in the esterification with a carboxylic acid.

When the 6-isopropenyl-3-methyl-3,9-decadienyl carboxylate compound (4) obtained has a sufficient purity, it may be used as such in a subsequent step. Alternatively, the crude product may be purified in any purification method used in usual organic synthesis, such as distillation or various chromatography. Distillation is particularly preferred in view of the industrial economy.

[4] Step A

Step A to synthesize a 2-methyl-2,6-heptadiene compound (7) having a protected hydroxyl group at position 1 will be described below. The 2-methyl-2,6-heptadiene compound (7) having a protected hydroxyl group at position 1 may be obtained by converting a 4-pentenyltriphenylphosphonium halide compound (5) into phosphorus ylide (18) using a base, and then subjecting phosphorus ylide (18) to a Wittig reaction with a 2-propanone compound (6) having a protected hydroxyl group, as shown in the following reaction formula.

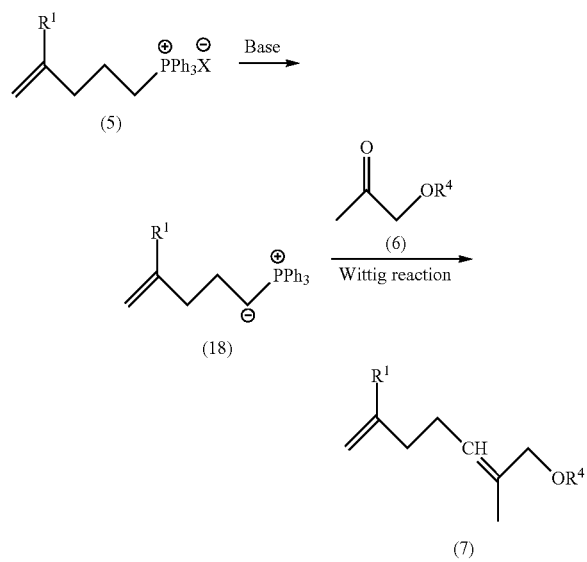

The 4-pentenyltriphenylphosphonium halide compound of the following formula (5) will be explained.

Here, $R^1$ is as defined for the formula (1). Ph represents a phenyl group. X is as defined for the formula (9).

Specific examples of the 4-pentenyltriphenylphosphonium halide compound (5) include 4-pentenyltriphenylphosphonium chloride, 4-pentenyltriphenylphosphonium bromide, 4-pentenyltriphenylphosphonium iodide, 4-methyl-4-pentenyltriphenylphosphonium chloride, 4-methyl-4-pentenyltriphenylphosphonium bromide, and 4-methyl-4-pentenyltriphenylphosphonium iodide.

The 4-pentenyltriphenylphosphonium halide compound (5) may be prepared by reacting a 4-pentenyl halide compound of the following formula (19) with triphenylphosphine ($PPh_3$) in a solvent according to the following reaction formula.

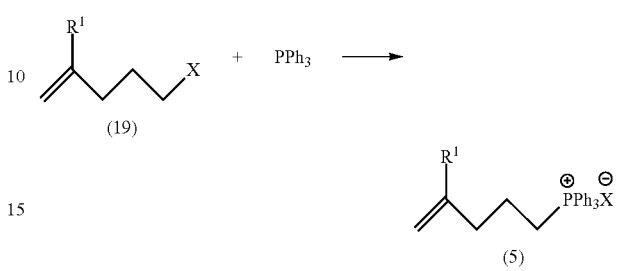

In the preparation of the 4-pentenyltriphenylphosphonium halide compound (5) according to the reaction formula, a metal halide and/or a quaternary onium salt may be incorporated in the reaction mixture to accelerate the reaction. Examples of the metal halide include lithium iodide, sodium iodide, potassium iodide, lithium bromide, sodium bromide, and potassium bromide. Examples of the quaternary onium salt include tetraethylammonium bromide, tetrabutylammonium bromide, tetrabutylphosphonium bromide, tetraethylammonium iodide, tetrabutylammonium iodide, and tetrabutylphosphonium iodide.

If the reaction system for preparing the 4-pentenyltriphenylphosphonium halide compound (5) becomes acidic, an isomer that has an internal double bond shifted from the terminal may be by-produced. To suppress the isomerization, the reaction mixture is preferably made basic by adding one or more bases selected from bicarbonates such as lithium bicarbonate, sodium bicarbonate, and potassium bicarbonate; carbonates such as lithium carbonate, sodium carbonate, and potassium carbonate; hydroxide salts such as lithium hydroxide, sodium hydroxide, and potassium hydroxide; and organic bases such as triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine, and morpholine. Potassium carbonate is particularly preferred in view of the economy and/or efficient suppression of isomerization.

The solvent used in the preparation of the 4-pentenyltriphenylphosphonium halide compound (5) may be same as that used in the preparation of phosphorus ylide (18) and a Wittig reaction described below.

An amount of the solvent is preferably from 10 g to 10,000 g, per mol of the 4-pentenyltriphenylphosphonium halide compound (5).

A reaction temperature in the preparation of the 4-pentenyltriphenylphosphonium halide compound (5) varies, depending on reaction conditions, and may be from −10° C. to 180° C., preferably from 0° C. to 160° C., more preferably from 10° C. to 140° C.

A reaction time in the preparation of the 4-pentenyltriphenylphosphonium halide compound (5) may be arbitrarily set. In view of the yield, it is desirable to monitor progress of the reaction with gas chromatography (GC) or thin layer chromatography (TLC) to complete the reaction. The reaction time is typically and preferably from about 0.5 to 60 hours.

The 2-propanone compound of the following formula (6) having a protected hydroxyl group will be described.

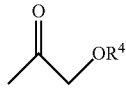
(6)

Here, $R^4$ represents a protective group for a hydroxyl group. The protective group may be appropriately selected from known protective groups for a hydroxyl group, which protective groups are stable during the reaction, post-treatments, and storage and are easily removed for deprotection. Examples of the appropriate protective group $R^4$ include oxyalkyl groups such as a methoxymethyl group, a 2-methoxyethoxymethyl group, a benzyloxymethyl group, a p-methoxybenzyloxymethyl group, a 2,2,2-trichloroethoxymethyl group, a 1-ethoxyethyl (EE) group, and a tetrahydropyranyl (THP) group, and isomers thereof. A part of the hydrogen atoms in these protective groups may be substituted with a methyl group or an ethyl group. Other protective groups include, for example, acyl groups such as an acetyl group, a propionyl group, a butyryl group, an isobutyryl group, a propioloyl group, an acryloyl group, and a benzoyl group; and trialkylsilyl groups such as a trimethylsilyl (TMS) group, a triethylsilyl group, a triisopropylsilyl group, and a t-butyldimethylsilyl group; monoalkyldiarylsilyl groups such as a t-butyldiphenylsilyl group; and isomers thereof. A part of the hydrogen atoms in the acyl group and the silyl group may be substituted with a methyl group, an ethyl group, or a halogen atom. Examples of the halogen atom include a chlorine atom, a bromine atom, and an iodine atom.

The protective group $R^4$ is preferably a tetrahydropyranyl group, a 1-ethoxyethyl group, or a trimethylsilyl group in view of the reactivity and/or economy. When the protective group $R^4$ is a trimethylsilyl group, removal of the protective group may occur during the Wittig reaction. However, this removal of the protective group does not matter, because the deprotection is planned to be carried out in a subsequent step.

The 2-propanone compound (6) having a protected hydroxyl group may be commercially available one or may be prepared from hydroxyacetone according to any known method.

The 2-methyl-2,6-heptadiene compound of the following formula (7) having a protected hydroxyl group at position 1 will be explained.

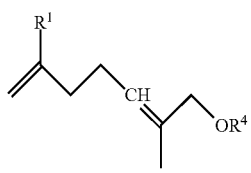
(7)

Here, $R^1$ is as defined for the formula (1), and $R^4$ is as defined for the formula (6).

The 2-methyl-2,6-heptadiene compound (7) having a protected hydroxyl group at position 1 may be a (Z)-2-methyl-2,6-heptadiene compound of the following formula (7a) having a protected hydroxyl group at position 1, or an (E)-2-methyl-2,6-heptadiene compound of the following formula (7b) having a protected hydroxyl group at position 1. The 2-methyl-2,6-heptadiene compound (7) having a protected hydroxyl group at position 1 may be either a single isomer or a combination of the isomers.

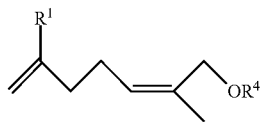
(7a)

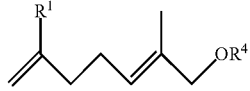
(7b)

The Wittig reaction may be carried out by adding a base to the 4-pentenyltriphenylphosphonium halide compound (5) in a solvent to form phosphorus ylide (18), and then adding the 2-propanone compound (6) having a protected hydroxyl group, if necessary, with heating or cooling.

Examples of the base used in the preparation of phosphorus ylide (18) include metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide; organometallic reagents such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; and metal hydrides such as sodium hydride, potassium hydride, and calcium hydride.

The base may be used either alone or in combination thereof and is chosen in view of the reactants and/or reactivity and/or selectivity.

An amount of the base used in the preparation of the phosphorus ylide is preferably from 0.7 mol to 5 mol, per mol of the 4-pentenyltriphenylphosphonium halide compound (5).

A solvent used in the preparation of the phosphorus ylide may be same as that used in a Wittig reaction described below.

A reaction temperature in the preparation of phosphorus ylide (18) is preferably from −78 to 50° C., more preferably from −78° C. to 35° C.

A reaction time in the preparation of phosphorus ylide (18) is preferably from 5 minutes to 18 hours, more preferably from 5 minutes to 10 hours, in view of the stability of the reagents.

An amount of the 2-propanone compound (6) having a protected hydroxyl group used in the Wittig reaction is preferably from 0.6 mol to 5 mol, per mol of the 4-pentenyltriphenylphosphonium halide compound (5).

Examples of the solvent used in the Wittig reaction include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

An amount of the solvent is preferably from 10 g to 10,000 g, per mol of the 4-pentenyltriphenylphosphonium halide compound (5).

A reaction temperature of the Wittig reaction is preferably from −78° C. to 50° C., more preferably from −50° C. to 35° C.

A reaction time of the Wittig reaction may be arbitrarily set. In view of the yield, it is desirable to monitor progress of the reaction with gas chromatography (GC) and/or thin layer chromatography (TLC) to complete the reaction. The reaction time is typically and preferably from about 0.5 to 24 hours.

When the 2-methyl-2,6-heptadiene compound (7) having a protected hydroxyl group at position 1 obtained in the Wittig reaction has a sufficient purity, it may be used as such in a subsequent step. Alternatively, the crude product may be purified in any purification method used in usual organic synthesis, such as distillation or various chromatography. Distillation is particularly preferred in view of the industrial economy.

[5] Step B

Step B to synthesize a 2-methyl-2,6-heptadienol compound (8) will be described below. The 2-methyl-2,6-heptadienol compound (8) may be obtained by removing the protective group from the 2-methyl-2,6-heptadiene compound (7) having a protected hydroxyl group at position 1 which was obtained in step A, as shown in the following reaction formula.

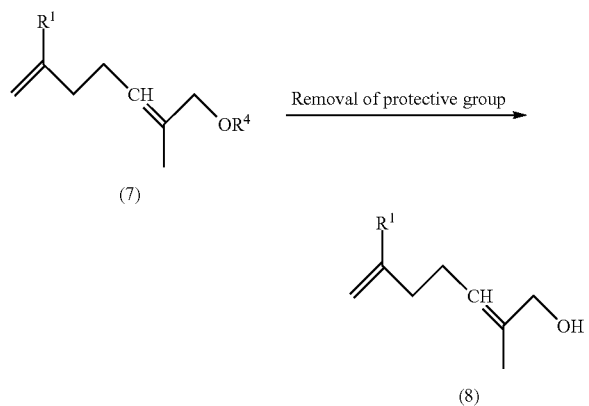

The 2-methyl-2,6-heptadienol compound of the following formula (8) will be explained.

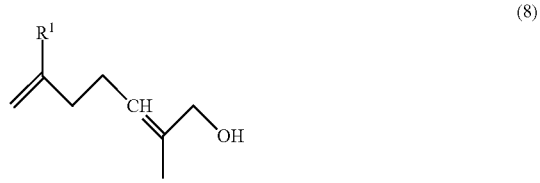

Here, $R^1$ is as defined for the formula (1).

The 2-methyl-2,6-heptadienol compound (8) may be a (Z)-2-methyl-2,6-heptadienol compound of the following formula (8a) or an (E)-2-methyl-2,6-heptadienol compound of the following formula (8b). The 2-methyl-2,6-heptadienol compound (8) may be either a single isomer or a combination of the isomers.

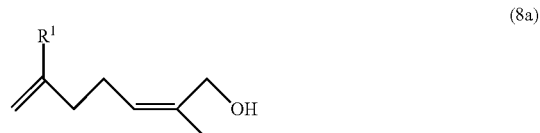

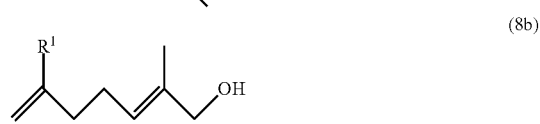

Removal conditions of the protective group may be appropriately selected, depending upon a type of the protective group in the 2-methyl-2,6-heptadiene compound (7) having a protected hydroxyl group at position 1. For example, when the protective group is an oxyalkyl group such as a methoxymethyl group, removal of the protective group may be conducted by solvolysis with an acid. When the protective group is an acyl group, removal of the protective group may be conducted by, for instance, solvolysis with an acid or a base. When the protective group is a silyl group such as a t-butyldimethylsilyl group, removal of the protective group may be conducted by solvolysis with an acid as well as by fluoride ions.

For the removal of the protective group with an acid, the 2-methyl-2,6-heptadienol compound (8) is obtained by adding an acid and, if necessary, water or a solvent to the 2-methyl-2,6-heptadiene compound (7) having a protected hydroxyl group at position 1, followed by cooling or heating.

Examples of the acid used in the removal of the protective group include inorganic acids such as hydrochloric acid, hydrobromic acid, hydroiodic acid, sulfuric acid, nitric acid, and phosphoric acid, or salts thereof, organic acids such as formic acid, acetic acid, propionic acid, oxalic acid, trifluoroacetic acid, methanesulfonic acid, benzenesulfonic acid, p-toluenesulfonic acid, and naphthalenesulfonic acid, or salts thereof, Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethylsilyl iodide; oxides such as alumina, silica, and titania; and minerals such as montmorillonite.

The acid is preferably acetic acid in view of the economy and/or reactivity.

The acid may be used alone or in combination thereof, if necessary. The acid may be commercially available one.

An amount of the acid is preferably small in view of the economy and may be arbitrarily set as long as a practically sufficient reaction rate is achieved. An amount of the acid is preferably from 0.00001 to 10,000 mol, more preferably from 0.0001 to 1,000 mol, and even more preferably from 0.001 to 100 mol, per mol of the 2-methyl-2,6-heptadiene compound (7) having a protected hydroxyl group at position 1.

When water is used in the removal of the protective group with an acid, an amount of the water is preferably from 1 to 10,000 mol, more preferably from 1 to 1,000 mol, and even more preferably from 1 to 500 mol, per mol of the 2-methyl-2,6-heptadiene compound (7) having a protected hydroxyl group at position 1. The reaction may be carried out while removing, from the reaction system, an alcohol produced in the removal of the protective group, for instance, by distillation.

Examples of the solvent used in the removal of the protective group with the acid include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

An amount of the solvent is preferably from 10 g to 10,000 g, per mol of the 2-methyl-2,6-heptadiene compound (7) having a protected hydroxyl group at position 1.

A reaction temperature of the removal of the protective group with the acid varies, depending on reaction conditions, and is preferably from −78° C. to 160° C., more preferably from −50° C. to 140° C., and even more preferably from −30° C. to 120° C.

A reaction time of the removal of the protective group with the acid may be arbitrarily set. In view of the yield, it is desirable to monitor progress of the reaction with gas chromatography (GC) and/or thin layer chromatography (TLC) to complete the reaction. The reaction time is typically from about 0.5 to 24 hours.

For the removal of the protective group with a base, the 2-methyl-2,6-heptadienol compound (8) is obtained by adding a base and, if necessary, water or a solvent to the 2-methyl-2,6-heptadiene compound (7) having a protected hydroxyl group at position 1, followed by cooling or heating.

Examples of the base used in the removal of the protective group include alkoxides such as sodium methoxide, sodium ethoxide, lithium methoxide, lithium ethoxide, potassium methoxide, and potassium ethoxide; and hydroxide salts such as sodium hydroxide, lithium hydroxide, potassium hydroxide, and barium hydroxide.

The base is preferably sodium hydroxide in view of the economy and/or reactivity.

The base may be used alone or in combination thereof, if necessary. The base may be commercially available one.

An amount of the base is preferably small in view of the economy and may be arbitrarily set as long as a practically sufficient reaction rate is achieved. An amount of the base is preferably from 0.00001 to 10,000 mol, more preferably from 0.0001 to 1,000 mol, and even more preferably from 0.001 to 100 mol, per mol of the 2-methyl-2,6-heptadiene compound (7) having a protected hydroxyl group at position 1.

When water is used in the removal of the protective group with the base, an amount of the water is preferably from 1 to 10,000 mol, more preferably from 1 to 1,000 mol, and even more preferably from 1 to 500 mol, per mol of the 2-methyl-2,6-heptadiene compound (7) having a protected hydroxyl group at position 1.

Examples of the solvent used in the removal of the protective group with the base include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

For the selection of the base and solvent, use of an alkoxide as a base in a solvent containing water and use of a hydroxide salt as a base in a solvent containing an alcohol are thought to provide identical conditions in the reaction system.

An amount of the solvent is preferably from 10 g to 10,000 g, per mol of the 2-methyl-2,6-heptadiene compound (7) having a protected hydroxyl group at position 1.

A reaction temperature of the removal of the protective group with the base varies, depending on reaction conditions, and is preferably from −78° C. to 160° C., more preferably from −50° C. to 140° C., and even more preferably from −30° C. to 120° C.

A reaction time of the removal of the protective group with the base may be arbitrarily set. In view of the yield, it is desirable to monitor progress of the reaction with gas chromatography (GC) and/or thin layer chromatography (TLC) to complete the reaction. The reaction time is typically from about 0.5 to 24 hours.

When the protective group is a silyl group, and removal of the protective group is conducted with fluoride ions, the 2-methyl-2,6-heptadienol compound (8) may be obtained by adding a reagent that can work as a fluoride ion source and, if necessary, a solvent to the 2-methyl-2,6-heptadiene compound (7) having a protected hydroxyl group at position 1, followed by cooling or heating. This removal of the protective group may also be carried out in combination with incorporation of the acid mentioned for the removal of the protective group with an acid.

Examples of the reagent that can work as a fluoride ion source include inorganic acids such as hydrofluoric acid; amine complexes such as pyridine-nHF and triethylamine-nHF; inorganic salts such as cesium fluoride, potassium fluoride, lithium tetrafluoroborate ($LiBF_4$), and ammonium fluoride; and organic salts such as tetrabutylammonium fluoride (TBAF).

The reagent that can work as a fluoride ion source may be used alone or in combination thereof, if necessary. The reagent that can work as a fluoride ion source may be commercially available one.

An amount of the reagent in the removal of the protective group with fluoride ions is preferably from 0.1 to 500 mol, more preferably from 0.1 to 50 mol, per mol of the 2-methyl-2,6-heptadiene compound (7) having a protected hydroxyl group at position 1.

The solvent, an amount of the solvent, a reaction time, and a reaction temperature in the removal of the protective group with fluoride ions may be same as those mentioned for the removal of the protective group of the 2-methyl-2,6-heptadiene compound (7) having a protected hydroxyl group at position 1 with an acid.

When the 2-methyl-2,6-heptadienol compound (8) obtained in the removal of the protective group has a sufficient purity, it may be used as such in a subsequent step. Alternatively, the crude product may be purified in any purification method used in usual organic synthesis, such as distillation or various chromatography. Distillation is particularly preferred in view of the industrial economy.

In step A, the 4-pentenyltriphenylphosphonium halide compound (5) is reacted with a base to form phosphorus ylide (18), and then phosphorus ylide (18) is subjected to a Wittig reaction with the 2-propanone compound (6) having a protected hydroxyl group to form the 2-methyl-2,6-heptadiene compound (7) having a protected hydroxyl group at position 1. The removal of the protective group may occur subsequently to the Wittig reaction in the conditions of the Wittig reaction in step A, so that the 2-methyl-2,6-heptadienol compound (8) may be obtained without step B. Thus, when the removal of the protective group occurs subsequently to the Wittig reaction in step A, the 2-methyl-2,6-heptadienol compound (8) is produced. When the removal of the protective group occurs on a part of the 2-methyl-2,6-heptadiene compound (7) having a protected hydroxyl group at position 1, a mixture of the 2-methyl-2,6-heptadiene compound (7) having a protected hydroxyl group at position 1 and a 2-methyl-2,6-heptadienol compound (8) is produced. Whether the removal of the protective group occurs or not subsequently to the Wittig reaction depends on, for instance, a type of a protective group.

[6] Step C

Step C to synthesize the 3-isopropenyl-6-heptenoate ester compound (1) will be described below. The 3-isopropenyl-6-heptenoate ester compound (1) may be obtained by subjecting the 2-methyl-2,6-heptadienol compound (8) obtained in step B to a Johnson-Claisen rearrangement with an orthoacetate ester compound (11), as shown in the following reaction formula.

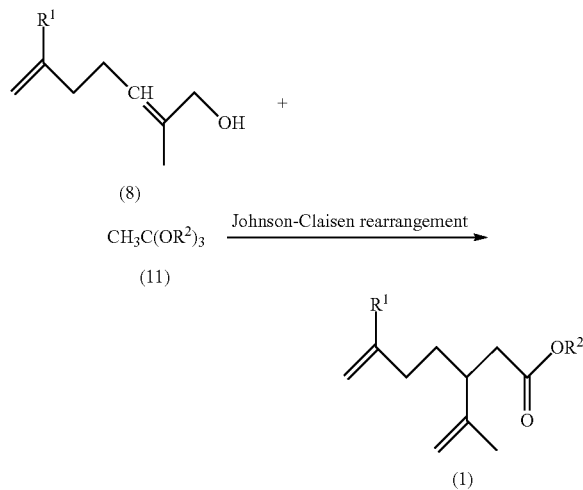

The Johnson-Claisen rearrangement may be carried out by adding an acid to a mixture of the 2-methyl-2,6-heptadienol compound (8) and an orthoacetate ester (11) in the presence or absence of a solvent, if necessary, with heating.

Examples of the acid used in the Johnson-Claisen rearrangement include mineral acids such as hydrochloric acid, hydrobromic acid, sulfuric acid, and nitric acid; organic acids such as acetic acid, propionic acid, oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium(IV) methoxide, titanium(IV) ethoxide, titanium(IV) isopropoxide, and titanium(IV) oxide.

The acid is preferably propionic acid in view of the reactivity and/or economy.

The acid may be used alone or in combination thereof, if necessary. The acid may be commercially available one.

An amount of the acid is preferably small in view of the economy and may be arbitrarily set as long as a practically sufficient reaction rate is achieved. An amount of the acid is preferably from 0.00001 to 10,000 mol, more preferably from 0.0001 to 100 mol, per mol of the 2-methyl-2,6-heptadienol compound (8).

The orthoacetate ester compound of the following formula (11) will be explained.

Here, $R^2$ in the orthoacetate ester is as defined for the formula (1).

An amount of the orthoacetate ester used is preferably from 1 to 10,000 mol, more preferably from 1 to 100 mol, per mol of the 2-methyl-2,6-heptadienol compound (8) in view of the economy.

Examples of the solvent used in the Johnson-Claisen rearrangement include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

The Johnson-Claisen rearrangement is preferably carried out without any solvent in view of the economy and/or reactivity.

A reaction temperature of the Johnson-Claisen rearrangement varies, depending on reaction conditions, and is preferably from −78° C. to 300° C., more preferably from 0° C. to 300° C., and even more preferably from 0° C. to 200° C.

A reaction time of the Johnson-Claisen rearrangement may be arbitrarily set. In view of the yield, it is desirable to monitor progress of the reaction with gas chromatography (GC) and/or thin layer chromatography (TLC) to complete the reaction. The reaction time is typically from about 1 to 100 hours.

In step B, the 2-methyl-2,6-heptadiene compound (7) having a protected hydroxyl group at position 1 is subjected to removal of the protective group to form a 2-methyl-2,6-heptadienol compound (8). The rearrangement reaction occurs subsequently to the removal of the protective group in step B in the conditions of the removal of the protective group, so that the 3-isopropenyl-6-heptenoate ester compound (1) may be obtained without step C. Thus, the rearrangement reaction occurs subsequently to the removal of the protective group in step B, so that the 3-isopropenyl-6-heptenoate ester compound (1) is produced. Alternatively, when the rearrangement reaction occurs on a part of the 2-methyl-2,6-heptadiene compound (7) having a protected hydroxyl group at position 1, a mixture of the 2-methyl-2,6-heptadienol compound (8) and the 3-isopropenyl-6-heptenoate ester compound (1) is produced. Whether the rearrangement reaction occurs or not subsequently to the removal of the protective group depends on, for example, a type of the protective group.

When the 3-isopropenyl-6-heptenoate ester compound (1) obtained above has a sufficient purity, it may be used as such in a subsequent step. Alternatively, the crude product may be purified in any purification method used in usual organic synthesis, such as distillation or various chromatography. Distillation is particularly preferred in view of the industrial economy.

Thus, the present invention provides the process for efficiently and industrially preparing the 6-isopropenyl-3-methyl-3,9-decadienyl carboxylate compound (4) without an oxidation reaction that is industrially unfavorable in view of safety, economy, and environmental burdens. The present invention also provides the process for preparing the 3-isopropenyl-6-heptenal compound (2) which is a useful intermediate in the preparation of the 6-isopropenyl-3-methyl-3,9-decadienyl carboxylate compound (4). The present invention also provides the 3-isopropenyl-6-methyl-6-heptenoate ester compound (1') which is a useful intermediate in the preparation of the 6-isopropenyl-3,9-dimethyl-3,9-decadienyl carboxylate compound (4).

EXAMPLES

The present invention will be further described with reference to the following Examples. It should be understood that the present invention is not limited to or by the following Examples.

The term "purity" as used herein means an area percentage obtained by gas chromatography (GC), unless otherwise specified. The term "production ratio" is a ratio of area percentages obtained by GC. The term "yield" is calculated from the area percentages obtained by GC.

In the Examples, monitoring of the reactions was carried out in the following GC conditions.

GC conditions: GC: Capillary gas chromatograph GC-2014 (Shimadzu Corporation); column: DB-5, 0.25 μm×0.25 mmϕ×30 m; carrier gas: He (1.55 mL/min), detector: FID; column temperature: 100° C., elevated in a rate of 10° C./min, and up to 230° C.

The yield was calculated according to the following equation in consideration of purities (% GC) of a starting material and a product.

Yield (%)={[(weight of a product obtained by a reaction×% GC)/molecular weight of a product]+[(weight of a starting material in a reaction×% GC)/molecular weight of a starting material]}×100

The term "crude yield" refers to a yield of a crude product obtained without purification.

Example 1: Synthesis of a 2-methyl-2,6-heptadiene Compound Having a Protected Hydroxyl Group at Position 1 (7: $R^1$=H, $R^4$=THP)

(19: $R^1$ = H, X = Br)

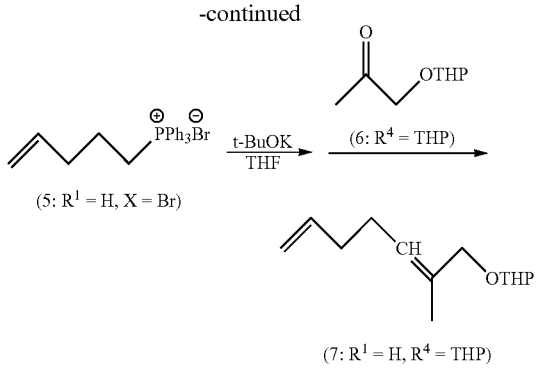

In a reactor were placed a 4-pentenyl halide compound (19: $R^1$=H, X=Br) (223.55 g: 1.50 mol), triphenylphosphine (PPh$_3$) (491.79 g: 1.87 mol), and dimethylformamide (DMF) (306 g) in a nitrogen atmosphere and stirred at 100° C. for 12 hours to prepare a 4-pentenyltriphenylphosphonium halide compound (5: $R^1$=H, X=Br). The temperature of the mixture was then lowered to room temperature (20 to 25° C.), and tetrahydrofuran (THF) (1080 g) was added. The mixture was cooled to a temperature of 0 to 5° C., and t-butoxy potassium (t-BuOK) (176.87 g: 1.57 mol) was added and stirred for 1 hour. Then, the mixture was cooled to a temperature of 0° C., and a 2-propanone compound having a protected hydroxyl group (6: $R^4$=THP) (282.00 g: 1.37 mol) was added dropwise over 100 minutes. The mixture was stirred at a solution temperature of 10 to 15° C. for 1 hour. Pure water (750 g) was then added to the reaction mixture and stirred for 30 minutes, and the organic phase was separated. The separated organic phase was subjected to post-treatment, i.e., usual washing and concentration, and hexane (900 g) was added to the resulting solution and stirred for 30 minutes. The mixture was subjected to filtration and concentration to obtain a crude product of the target compound, 2-methyl-2,6-heptadiene compound having a protected hydroxyl group at position 1 (7: $R^1$=H, $R^4$=THP) (487.44 g) in a crude yield of 85.57%.

2-Methyl-2,6-heptadiene compound (7: $R^1$=H, $R^4$=THP) having a protected hydroxyl group at position 1

IR (D-ATR): ν=3077, 2941, 2871, 2851, 1641, 1253, 1441, 1376, 1353, 1321, 1262, 1201, 1183, 1158, 1134, 1118, 1078, 1053, 1023, 979, 908, 870, 816, 642 cm-1.

$^1$H-NMR (500 MHz, CDCl$_3$): 1.48-1.73 (5H, m), 1.76-1.77 (3H, m), 1.77-1.89 (1H, m), 2.05-2.18 (4H, m), 3.47-3.53 (1H, m), 3.84-3.90 (1H, m), 4.05-4.12 (2H, m), 4.58 (1H, t-like, J=3.5 Hz), 4.93-5.03 (2H, m), 5.36 (1H, t-like, J=6.9 Hz), 5.76-5.84 (1H, m) ppm.

$^{13}$C-NMR (125 MHz, CDCl$_3$): δ=19.49, 21.70, 25.74, 27.07, 30.64, 34.02, 62.12, 65.36, 97.48, 114.67, 126.75, 132.19, 138.27.

GC-MS (EI, 70 eV): 29, 41, 55, 67, 85, 97, 109, 126, 138, 155, 168, 181, 195, 210.

Example 2: Synthesis of a 2-methyl-2,6-heptadiene Compound Having a Protected Hydroxyl Group at Position 1 (7: $R^1$=H, $R^4$=TMS)

(19: $R^1$ = H, X = Br)

-continued

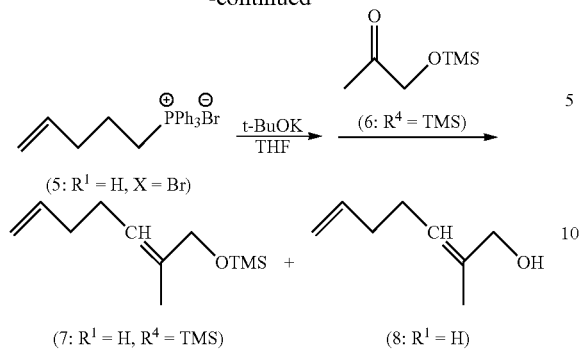

In a reactor were placed a 4-pentenyl halide compound (19: $R^1$=H, X=Br) (271.26 g: 1.80 mol), triphenylphosphine (PPh$_3$) (495.73 g: 1.89 mol), and dimethylformamide (DMF) (630 g) in a nitrogen atmosphere and stirred at 100° C. for 12 hours to prepare a 4-pentenyltriphenylphosphonium halide compound (5: $R^1$=H, X=Br). The temperature of the mixture was then lowered to room temperature (50 to 60° C.), and tetrahydrofuran (THF) (1296 g) was added. The mixture was cooled to a temperature of 0 to 5° C., and t-butoxy potassium (t-BuOK) (208.20 g: 1.85 mol) was added and stirred for 1 hour. Then, the mixture was cooled to a temperature of 0 to 5° C., and a 2-propanone compound having a protected hydroxyl group (6: $R^4$=THP) (242.02 g: 1.64 mol) was added dropwise over 180 minutes. The mixture was stirred at a solution temperature of 10 to 15° C. for 1 hour. Pure water (900 g) was then added to the reaction mixture and stirred for 30 minutes, and the organic phase was separated. The separated organic phase was subjected to post-treatment, i.e., usual washing and concentration, and hexane (1500 g) was added to the resulting solution and stirred for 30 minutes. The mixture was subjected to filtration and concentration to obtain a crude product (207.41 g) containing the target compound, 2-methyl-2,6-heptadiene compound (7: $R^1$=H, $R^4$=TMS) having a protected hydroxyl group at position 1, and a 2-methyl-2,6-heptadienol compound (8: $R^1$=H) in a crude yield of 45.30%. A portion of the crude product was purified to separate a 2-methyl-2,6-heptadiene compound having a protected hydroxyl group at position 1 (7: $R^1$=H, $R^4$=TMS), and various spectrum data were determined. The results of the spectrum data were shown below.

2-Methyl-2,6-heptadiene compound (7: $R^1$=H, $R^4$=TMS) having a protected hydroxyl group at position 1

IR (D-ATR): ν=3079, 2958, 2918, 2852, 1641, 1436, 1380, 1251, 1069, 992, 961, 912, 879, 841, 747, 685 cm-1.

$^1$H-NMR (500 MHz, CDCl$_3$): δ=0.13 (9H, s), 1.74 (3H, s-like), 2.06-2.16 (4H, m), 4.11 (2H, s), 4.94-5.04 (2H, m), 5.24 (OH, t-like, J=6.8 Hz), 5.77-5.85 (OH, m) ppm.

$^{13}$C-NMR (125 MHz, CDCl$_3$): δ=−0.43, 21.14, 27.03, 34.03, 61.19, 114.67, 126.44, 134.74, 138.31 ppm.

GC-MS (EI, 70 eV): 27, 41, 59, 73, 93, 108, 127, 143, 157, 169, 183, 198.

Example 3: Synthesis of a 2-methyl-2,6-heptadiene Compound Having a Protected Hydroxyl Group at Position 1 (7: $R^1$=H, $R^4$=EE)

-continued

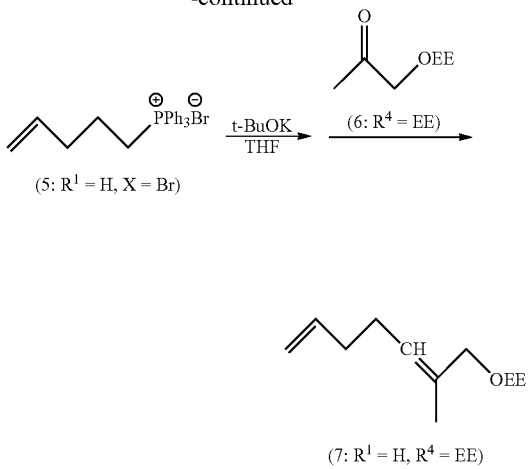

In a reactor were placed a 4-pentenyl halide compound (19: $R^1$=H, X=Br) (271.26 g: 1.80 mol), triphenylphosphine (PPh$_3$) (476.84 g: 1.82 mol), and dimethylformamide (DMF) (630 g) in a nitrogen atmosphere and stirred at 100° C. for 24 hours to prepare a 4-pentenyltriphenylphosphonium halide compound (5: $R^1$=H, X=Br). The temperature of the mixture was then lowered to room temperature (50 to 60° C.), and tetrahydrofuran (THF) (1602 g) was added. The mixture was cooled to a temperature of 0 to 5° C., and t-butoxy potassium (t-BuOK) (212.25 g: 1.89 mol) was added and stirred for 1 hour. Then, the mixture was cooled to a temperature of 0 to 5° C., and a 2-propanone compound having a protected hydroxyl group (6: $R^4$=EE) (241.63 g: 1.64 mol) was added dropwise over 100 minutes. The mixture was stirred at a solution temperature of 10 to 15° C. for 1 hour. Pure water (900 g) was then added to the reaction mixture and stirred for 30 minutes, and the organic phase was separated. The separated organic phase was subjected to post-treatment, i.e., usual washing and concentration, and hexane (1500 g) was added to the resulting solution and stirred for 30 minutes. The mixture was subjected to filtration and concentration to obtain a crude product of the target compound, 2-methyl-2,6-heptadiene compound having a protected hydroxyl group at position 1 (7: $R^1$=H, $R^4$=EE) (337.69 g). The crude product was subjected to distillation at a reduced pressure to obtain a purified 2-methyl-2,6-heptadiene compound having a protected hydroxyl group at position 1 (7: $R^1$=H, $R^4$=EE) (252.38 g: 1.23 mol). A yield calculated from the whole fractions including a fore-running fraction was 83.03%.

2-Methyl-2,6-heptadiene compound having a protected hydroxyl group at position 1 (7: $R^1$=H, $R^4$=EE)

IR (D-ATR): ν=3078, 2976, 2916, 1641, 1443, 1378, 1337, 1273, 1130, 1098, 1059, 1032, 985, 929, 912 cm-1.

$^1$H-NMR (500 MHz, CDCl$_3$): δ=1.20 (3H, t, J=7.1 Hz), 1.31 (3H, d, J=5.4 Hz), 1.64-1.76 (3H, m), 2.06-2.20 (4H, m), 3.46-3.68 (2H, m), 3.97-4.09 (2H, m), 4.69 (OH, q, J=5.4 Hz), 4.92-5.03 (2H, m), 5.34-5.44 (OH, m), 5.74-5.85 (OH, m) ppm.

$^{13}$C-NMR (125 MHz, CDCl$_3$): δ=15.31, 19.73, 21.74, 27.11, 33.99, 60.22, 63.56, 98.80, 114.70, 128.44, 132.38, 138.20 ppm.

GC-MS (EI, 70 eV): 29, 45, 55, 73, 83, 93, 109, 126, 137, 152, 169, 183, 198.

Example 4: Synthesis of a 2-methyl-2,6-heptadiene Compound Having a Protected Hydroxyl Group at Position 1 (7: $R^1$=CH$_3$, $R^4$=EE)

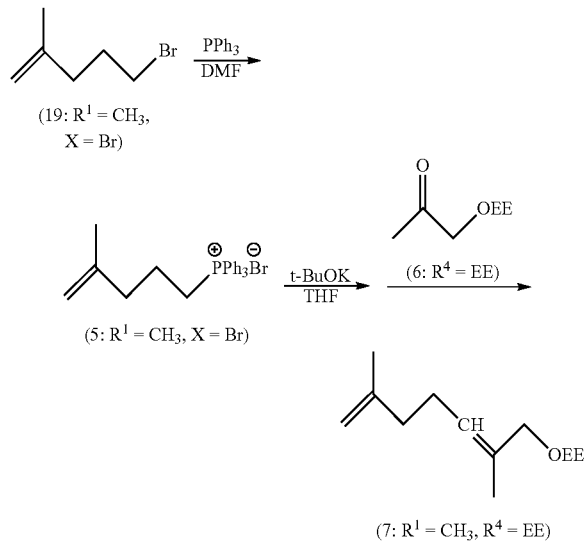

In a reactor were placed a 4-pentenyl halide compound (19: $R^1$=CH$_3$, X=Br) (90.00 g: 0.54 mol), triphenylphosphine (PPh$_3$) (143.32 g: 0.55 mol), potassium carbonate (11.22 g: 0.08 mol), and dimethylformamide (DMF) (189.35 g) in a nitrogen atmosphere and stirred at 80° C. for 24 hours to prepare a 4-pentenyltriphenylphosphonium halide compound (5: $R^1$=CH$_3$, X=Br). The temperature of the mixture was then lowered to room temperature (50 to 60° C.), and tetrahydrofuran (THF) (486.90 g) was added. The mixture was cooled to a temperature of 0 to 5° C., and t-butoxy potassium (t-BuOK) (61.36 g: 0.55 mol) was added and stirred for 1 hour. Then, a 2-propanone compound having a protected hydroxyl group (6: $R^4$=EE) (73.69 g: 0.49 mol) was added dropwise at an internal temperature of 0 to 5° C. over 55 minutes. The mixture was stirred at a solution temperature of 10 to 15° C. for 19 hours. Pure water (270.5 g) was then added to the reaction mixture and stirred for 30 minutes, and the organic phase was separated. The separated organic phase was subjected to post-treatment, i.e., usual washing and concentration, and hexane (1500 g) was added to the resulting solution and stirred for 30 minutes. The mixture was subjected to filtration and concentration to obtain a crude product of the target compound, 2-methyl-2,6-heptadiene compound having a protected hydroxyl group at position 1 (7: $R^1$=CH$_3$, $R^4$=EE) (157.82 g). The crude product was subjected to distillation at a reduced pressure to obtain a purified 2-methyl-2,6-heptadiene compound having a protected hydroxyl group at position 1 (7: $R^1$=CH$_3$, $R^4$=EE) (89.79 g: 0.37 mol) in a yield of 75.20%.

2-Methyl-2,6-heptadiene compound having a protected hydroxyl group at position 1 (7: $R^1$=CH$_3$, $R^4$=EE)

IR (D-ATR): ν=3075, 2974, 2935, 1743, 1711, 1687, 1650, 1445, 1376, 1338, 1274, 1130, 1097, 1086, 1059, 1030, 983, 946, 930, 886 cm-1.

$^1$H-NMR (500 MHz, CDCl$_3$): δ=1.20 (3H, t, J=7.1 Hz), 1.31 (3H, d, J=5.4 Hz), 1.71 (3H, s), 1.75-1.76 (3H, m), 2.01-2.11 (2H, m), 2.16-2.21 (2H, m), 3.45-3.72 (2H, m), 3.97-4.11 (2H, m), 4.66-4.71 (3H, m), 5.27-5.42 (1H, m) ppm.

$^{13}$C-NMR (125 MHz, CDCl$_3$): δ=15.30, 19.73, 21.73, 22.39, 25.89, 37.89, 60.21, 63.58, 98.81, 110.00, 128.68, 132.16, 145.32 ppm.

GC-MS (EI, 70 eV): 29, 45, 57, 73, 93, 107, 123, 140, 156, 168, 183, 197, 213.

Example 5: Synthesis of a 2-methyl-2,6-heptadienol Compound (8: $R^1$=H)

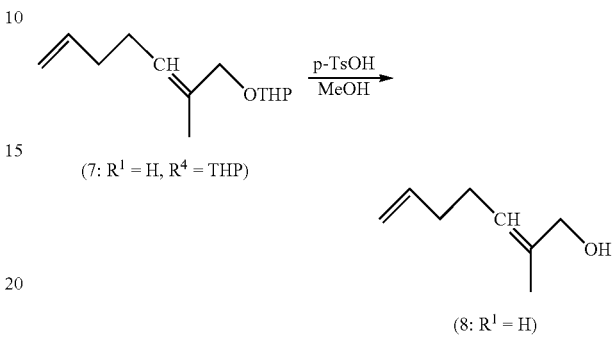

In a reactor were placed a 2-methyl-2,6-heptadiene compound having a protected hydroxyl group at position 1 (7: $R^1$=H, $R^4$=THP) (517.00 g: 1.287 mol) obtained as in Example 1, p-toluenesulfonic acid (p-TsOH) (33.24 g: 0.19 mol), and methanol (MeOH) (1287 g) in a nitrogen atmosphere and stirred at room temperature (20 to 25° C.) for 22 hours and 30 minutes. Then, sodium bicarbonate (21.62 g) and pure water (10 g) were added and stirred for 30 minutes. The reaction mixture was concentrated, and then hexane (500 g) and pure water (800 g) were added and stirred for 30 minutes. The organic phase was separated. The organic phase was concentrated, and then p-toluenesulfonic acid (33.24 g: 0.19 mol) and methanol (1287 g) were added and stirred at room temperature (20 to 25° C.) for 5 hours and 30 minutes. Then, sodium carbonate (50 g) and pure water (50 g) were added and stirred for 30 minutes. The reaction mixture was concentrated, and then hexane (1000 g) and pure water (1000 g) were added. The mixture was stirred for 30 minutes, and the organic phase was separated. The separated organic phase was subjected to post-treatment, i.e., usual washing and concentration, to obtain a crude product of the target compound, 2-methyl-2,6-heptadienol compound (8: $R^1$=H) (221.90 g) in a crude yield of 60.33%.

2-Methyl-2,6-heptadienol compound (8: $R^1$=H)

IR (D-ATR): ν=3325, 3079, 2969, 2920, 1641, 1439, 1416, 1378, 1321, 1246, 1005, 949, 912, 845, 761, 641 cm-1.

$^1$H-NMR (500 MHz, CDCl$_3$): 1.66 (1H, s-like), 1.78-1.79 (3H, m), 2.03-2.16 (4H, m), 4.10 (2H, s), 4.94-5.03 (2H, m), 5.28 (1H, t-like, J=6.9 Hz), 5.74-5.82 (OH, m) ppm.

$^{13}$C-NMR (125 MHz, CDCl$_3$): δ=21.20, 26.95, 33.93, 61.40, 114.91, 127.53, 134.77, 138.19 ppm.

GC-MS (EI, 70 eV): 29, 43, 57, 67, 79, 93, 108, 126.

Example 6: Synthesis of a 2-methyl-2,6-heptadienol Compound (8: $R^1$=H)

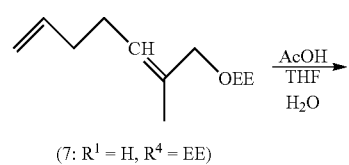

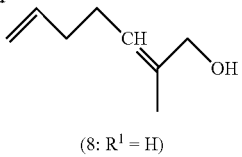

(8: R¹ = H)

In a reactor were placed a 2-methyl-2,6-heptadiene compound having a protected hydroxyl group at position 1 (7: R¹=H, R⁴=EE) (200 g: 0.965 mol) obtained as in Example 3, acetic acid (AcOH) (57.9 g: 0.965 mol), pure water (434.25 g), and tetrahydrofuran (THF) (434.25 g) in a nitrogen atmosphere and stirred at a temperature of 80 to 85° C. for 3 hours and 20 minutes while distilling off a distillate. The reaction mixture was cooled to 30 to 40° C., and pure water (675.5 g) and hexane (675.5 g) were added. The mixture was stirred for 30 minutes, and the organic phase was separated. The separated organic phase was subjected to post-treatment, i.e., usual washing and concentration, to obtain a crude product of the target compound, 2-methyl-2,6-heptadienol compound (8: R¹=H) (126.00 g) in a crude yield of 96.30%.

Example 7: Synthesis of a 2-methyl-2,6-heptadienol Compound (8: R¹=CH₃)

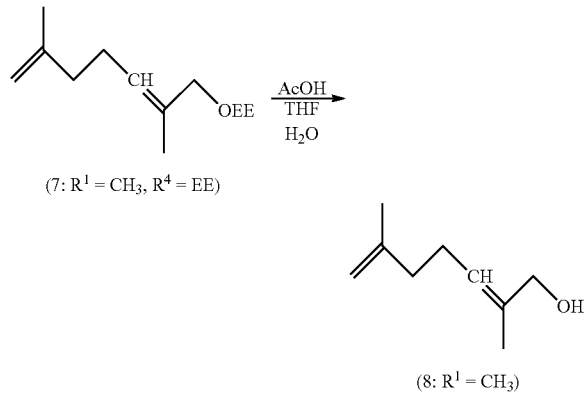

In a reactor were placed a 2-methyl-2,6-heptadiene compound having a protected hydroxyl group at position 1 (7: R¹=CH₃, R⁴=EE) (88.00 g: 0.363 mol) obtained as in Example 4, acetic acid (AcOH) (21.78 g: 0.363 mol), pure water (163.35 g), and tetrahydrofuran (THF) (163.35 g) in a nitrogen atmosphere and stirred at a temperature of 80 to 85° C. for 4 hours and 35 minutes while distilling off a distillate. The mixture was cooled to 30 to 40° C., and pure water (250.00 g) and hexane (250.00 g) were added. The mixture was stirred for 30 minutes, and the organic phase was separated. The separated organic phase was subjected to post-treatment, i.e., usual washing and concentration, to obtain a crude product of the target compound, 2-methyl-2,6-heptadienol compound (8: R¹=CH₃) (52.09 g). The crude product was subjected to distillation at a reduced pressure to obtain a purified 2-methyl-2,6-heptadienol compound (8: R¹=CH₃) (33.65 g: 0.23 mol). A yield calculated from the whole fractions including a fore-running fraction was 72.73%.

2-Methyl-2,6-heptadienol compound (8: R¹=CH₃)
IR (D-ATR): ν=3319, 3074, 2968, 2935, 2917, 1650, 1448, 1375, 1337, 1006, 948, 887 cm-1.
¹H-NMR (500 MHz, CDCl₃): 1.52 (1H, s), 1.71 (3H, s-like), 1.78-1.79 (3H, m), 2.01-2.07 (2H, m), 2.16-2.20 (2H, m), 4.11 (2H, s), 4.65-4.72 (2H, m), 5.28 (1H, t-like, J=7.1 Hz) ppm.
¹³C-NMR (125 MHz, CDCl₃): δ=21.20, 22.42, 25.74, 37.89, 61.45, 110.18, 127.82, 134.60, 145.37 ppm.
GC-MS (EI, 70 eV): 29, 43, 55, 67, 75, 84, 93, 107, 122, 132, 140.

Example 8: Synthesis of a 3-isopropenyl-6-heptenoate ester Compound (1: R¹=H, R²=

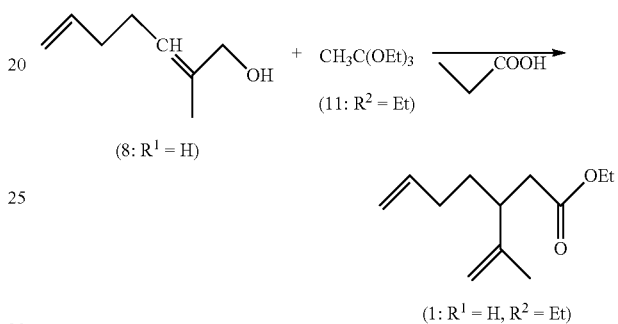

In a reactor were placed a 2-methyl-2,6-heptadienol compound (8: R¹=H) (60 g: 0.456 mol) obtained as in Example 6, an orthoacetate ester compound (11: R²=Et) (527.84 g: 3.192 mol), and propionic acid (4.5 g: 0.06 mol) in a nitrogen atmosphere and stirred at a temperature of 140° C. for 2 hours. Then, the reaction mixture was heated to a temperature of 150 to 160° C. while distilling off ethanol from the reaction mixture, and stirred for 6 hours. Then, the mixture was cooled to a temperature of 30 to 40° C., and sodium bicarbonate (30 g) and pure water (600 g) were added. The mixture was stirred for 30 minutes, and the organic phase was separated. The separated organic phase was subjected to post-treatment, i.e., usual washing, drying, and concentration, to obtain a crude product of the target compound, 3-isopropenyl-6-heptenoate ester compound (1: R¹=H, R²=Et) (169.76 g). The crude product was subjected to distillation at a reduced pressure to obtain a purified 3-isopropenyl-6-heptenoate ester compound (1: R¹=H, R²=Et) (69.32 g: 0.33 mol). A yield calculated from the whole fractions including a fore-running fraction was 80.70%.

3-Isopropenyl-6-heptenoate ester compound (1: R¹=H, R²=Et)
IR (D-ATR): ν=3077, 2979, 2932, 1737, 1642, 1445, 1370, 1338, 1252, 1157, 1113, 1036, 995, 910, 895, 636, 559 cm-1.
¹H-NMR (500 MHz, CDCl₃): δ=1.22 (3H, t, J=7.1 Hz), 1.45 (2H, q, J=7.6 Hz), 1.65 (3H, s-like), 1.90-2.06 (2H, m), 2.34 (2H, d, J=8.0 Hz), 2.60 (1H, quin, J=7.5 Hz), 4.09 (2H, q, J=7.1 Hz), 4.73-4.78 (2H, m), 4.92-5.01 (2H, m), 5.74-5.82 (1H, m) ppm.
¹³C-NMR (125 MHz, CDCl₃): δ=14.20, 18.44, 31.23, 31.99, 39.20, 43.17, 60.15, 112.30, 114.59, 138.34, 145.79, 172.65 ppm.
GC-MS (EI, 70 eV): 29, 41, 55, 69, 81, 93, 108, 122, 142, 155, 167, 181, 196.

Example 9: Synthesis of a 3-isopropenyl-6-heptenoate ester Compound (1: $R^1$=CH$_3$, $R^2$=Et)

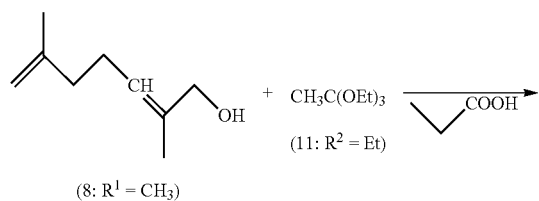

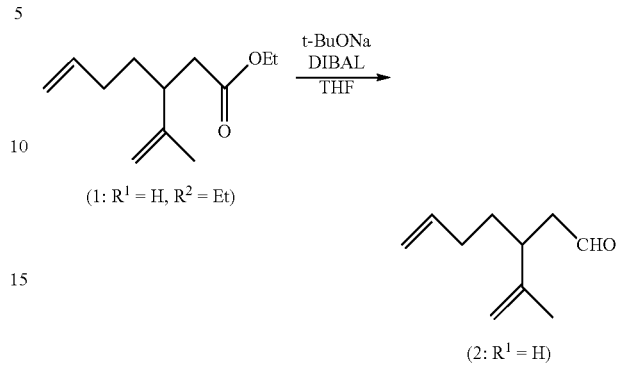

In a reactor were placed a 2-methyl-2,6-heptadienol compound (8: $R^1$=CH$_3$) (30 g: 0.206 mol) obtained as in Example 7 and an orthoacetate ester compound (11: $R^2$=Et) (167.10 g: 1.030 mol) in a nitrogen atmosphere, and propionic acid (2.06 g: 0.28 mol) was added dropwise over 5 minutes at a temperature of 100° C. The reactor temperature was raised to 140° C. Then, the reactor temperature was raised to 150 to 160° C., while distilling off ethanol from the reaction mixture, and the mixture was stirred for 7 hours and 30 minutes. Then, the mixture was cooled to a temperature of 20° C., and sodium bicarbonate (12.6 g), pure water (206 g), and hexane (100 g) were added and stirred for 30 minutes. The organic phase was separated. The separated organic phase was subjected to post-treatment, i.e., usual washing, drying, and concentration, to obtain a crude product of the target compound, 3-isopropenyl-6-heptenoate ester compound (1: $R^1$=CH$_3$, $R^2$=Et) (128.26 g). The crude product was subjected to distillation at a reduced pressure to obtain a purified 3-isopropenyl-6-heptenoate ester compound (1: $R^1$=CH$_3$, $R^2$=Et) (30.20 g: 0.129 mol). A yield calculated from the whole fractions including previous a fore-running fraction was 68.93%.

3-Isopropenyl-6-heptenoate ester compound (1: $R^1$=CH$_3$, $R^2$=Et)

IR (D-ATR): ν=3075, 2979, 2936, 1737, 1648, 1446, 1373, 1261, 1177, 1147, 1035, 889 cm-1.

$^1$H-NMR (500 MHz, CDCl$_3$): δ=1.22 (3H, t, J=7.3 Hz), 1.44-1.57 (2H, m), 1.65 (3H, s-like), 1.70 (3H, s), 1.87-1.97 (2H, m), 2.35 (2H, d, J=7.7 Hz), 2.57 (1H, quin-like, J=7.4 Hz), 4.10 (2H, q, J=7.1 Hz), 4.65-4.69 (2H, m), 4.73-4.78 (2H, m) ppm.

$^{13}$C-NMR (125 MHz, CDCl$_3$): δ=14.21, 18.50, 22.43, 30.74, 35.16, 39.25, 43.33, 60.15, 109.87, 112.27, 145.53, 145.90, 172.54 ppm.

GC-MS (EI, 70 eV): 29, 41, 55, 69, 81, 93, 107, 122, 142, 154, 167, 182, 196, 210.

Example 10: Synthesis of a 3-isopropenyl-6-heptenal Compound (2: $R^1$=H)

In a first reactor were placed t-butoxy sodium (t-BuONa) (20.28 g: 0.21 mol) and tetrahydrofuran (THF) (50 g) in a nitrogen atmosphere and stirred at 0° C. for 15 minutes. A hexane solution (200.2 mL) of aluminum diisobutyl hydride (DIBAL) (0.20 mol) was added dropwise to the reaction mixture over 105 minutes and then stirred at room temperature (20 to 25° C.) for 2 hours.

In a second reactor were placed a 3-isopropenyl-6-heptenoate ester compound (1: $R^1$=H, $R^2$=Et) (32.24 g: 0.154 mol) obtained as in Example 8 and THF (50 g) in a nitrogen atmosphere and cooled to −5 to 0° C. To this reaction mixture was added dropwise the solution prepared in the first reactor over 6 hours and 15 minutes and stirred at 0 to 5° C. for 4 hours. Then, an aqueous 20% hydrogen chloride solution (68.50 g) and pure water (300 g) were added, and the organic phase was separated. The separated organic phase was concentrated to obtain a crude product of the target compound, 3-isopropenyl-6-heptenal compound (2: $R^1$=H) (27.70 g) in a crude yield of 75.97%.

3-Isopropenyl-6-heptenal compound (2: $R^1$=H)

IR (D-ATR): ν=3076, 2975, 2928, 2858, 2720, 1726, 1642, 1441, 1416, 1377, 996, 897 cm-1.

$^1$H-NMR (500 MHz, CDCl$_3$): δ=1.41-1.54 (2H, m), 1.65 (3H, s-like), 1.92-2.06 (2H, m), 2.37-2.47 (2H, m), 2.66-2.72 (1H, m), 4.77-4.82 (2H, m), 4.93-5.02 (2H, m), 5.73-5.81 (1H, m), 9.65 (1H, t, J=2.3 Hz) ppm.

$^{13}$C-NMR (125 MHz, CDCl$_3$): δ=18.59, 31.10, 32.15, 40.88, 47.36, 112.68, 114.87, 138.07, 145.49, 202.22 ppm.

GC-MS (EI, 70 eV): 27, 41, 55, 69, 81, 95, 108, 123, 137, 151.

Example 11: Synthesis of a 3-isopropenyl-6-heptenal Compound (2: $R^1$=CH$_3$)

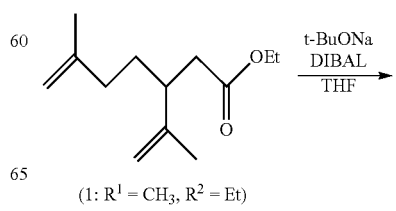

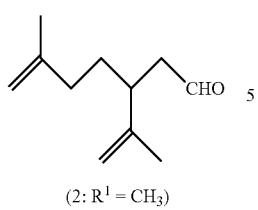

(2: R¹ = CH₃)

In a first reactor were placed t-butoxy sodium (t-BuONa) (12.51 g: 0.13 mol) and tetrahydrofuran (THF) (125 g) in a nitrogen atmosphere and stirred at 0 to 5° C. for 15 minutes. A hexane solution (121.08 mL) of aluminum diisobutyl hydride (DIBAL) (0.12 mol) was added dropwise to the reaction mixture over 105 minutes and then stirred at room temperature (20 to 25° C.) for 3 hours.

In a second reactor were placed a 3-isopropenyl-6-heptenoate ester compound (1: R¹=CH₃, R²=Et) (20.00 g: 0.09 mol) obtained as in Example 9 and THF (125 g) in a nitrogen atmosphere and cooled to −5 to 0° C. To this reaction mixture was added dropwise the solution prepared in the first reactor over 4 hours and 15 minutes and stirred at 0 to 5° C. for 4 hours. Then, an aqueous 20% hydrogen chloride solution (38.08 g), pure water (100 g), and hexane (100 g) were added, and the organic phase was separated. The separated organic phase was subjected to post-treatment, i.e., usual washing, drying, and concentration, to obtain a crude product of the target compound, 3-isopropenyl-6-heptenal compound (2: R¹=CH₃) (16.00 g) in a crude yield of 81.55%.

3-Isopropenyl-6-heptenal compound (2: R¹=CH₃)

IR (D-ATR): ν=3074, 2969, 2936, 2720, 1726, 1647, 1447, 1375, 1070, 1021, 890 cm-1.

¹H-NMR (500 MHz, CDCl₃): δ=1.47-1.55 (2H, m), 1.66 (3H, s-like), 1.70 (3H, s), 1.89-1.99 (2H, m), 2.38-2.48 (2H, m), 2.66 (1H, quin, J=7.3 Hz), 4.65-4.71 (2H, m), 4.77-4.82 (2H, m), 9.65 (1H, t-like, J=2.5 Hz) ppm.

¹³C-NMR (125 MHz, CDCl₃): δ=18.64, 22.40, 30.90, 35.04, 41.05, 47.41, 110.11, 112.65, 145.25, 145.61, 202.22 ppm.

GC-MS (EI, 70 eV): 29, 41, 55, 69, 81, 97, 107, 122, 137, 151, 165.

Example 12: Synthesis of a 6-isopropenyl-3-methyl-3,9-decadienol Compound (3: R¹=H)

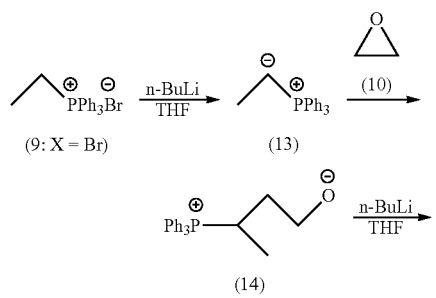

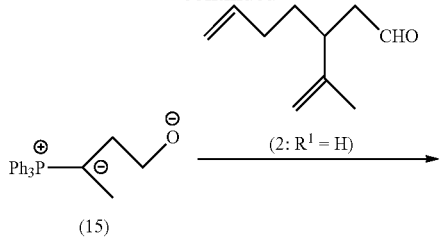

(2: R¹ = H)

(3: R¹ = H)

In a reactor were placed an ethyltriphenylphosphonium halide compound (9: X=Br) (5.79 g, 0.016 mol) and tetrahydrofuran (THF) (76 g) in a nitrogen atmosphere and cooled to 0 to 5° C. A hexane solution (5.89 ml) of n-butyl lithium (n-BuLi) (0.016 mol) was added dropwise to the reaction mixture over 15 minutes and then stirred for 15 minutes to prepare an ylide (13). Ethylene oxide (10) (0.69 g: 0.016 mol) was added dropwise to the reaction mixture over 30 minutes and stirred at 15 to 20° C. for 1 hour to prepare 3-triphenylphosphoniobutoxide (14). The reaction mixture was cooled to −20 to −15° C., and a hexane solution (5.15 ml) of n-butyl lithium (n-BuLi) (0.014 mol) was added dropwise over 10 minutes and then stirred for 15 minutes to prepare phosphorus ylide (15). The reaction mixture was cooled to −60 to −50° C., and a 3-isopropenyl-6-heptenal compound (2: R¹=H) (2.12 g: 0.013 mol) obtained as in Example 10 was added dropwise over 10 minutes. The temperature of the mixture was then raised to room temperature (20 to 25° C.) and stirred for 3 hours. Pure water (110 g) was added to the reaction mixture and stirred for 30 minutes, and the organic phase was separated. The separated organic phase was subjected to post-treatment, i.e., usual drying and concentration, to obtain a crude product of the target compound, 6-isopropenyl-3-methyl-3,9-decadienol compound (3: R¹=H) (3.52 g) in a crude yield of 92.31%.

6-Isopropenyl-3-methyl-3,9-decadienol compound (3: R¹=H)

IR (D-ATR): ν=3341, 3074, 2966, 2927, 1642, 1441, 1375, 1185, 1044, 995, 909, 890, 641, 559 cm-1.

¹H-NMR (500 MHz, CDCl₃): δ=1.31-1.49 (2H, m), 1.59-1.71 (7H, m), 1.88-2.16 (5H, m), 2.21-2.35 (2H, m), 3.59-3.67 (2H, m), 4.66-4.77 (2H, m), 4.91-5.01 (2H, m), 5.14-5.27 (1H, m), 5.75-5.83 (1H, m) ppm.

¹³C-NMR (125 MHz, CDCl₃): δ=15.76, 17.98, 18.44, 23.35, 31.58, 32.00, 32.09, 32.11, 35.16, 42.60, 47.14, 47.15, 59.60, 60.52, 111.70, 111.85, 114.27, 114.35, 126.80, 126.98, 131.46, 131.48, 138.83, 138.92, 147.13, 147.42 ppm.

GC-MS (EI, 70 eV): 29, 41, 55, 67, 81, 93, 107, 121, 135, 149, 163, 177, 193, 208.

Example 13: Synthesis of a 6-isopropenyl-3-methyl-3,9-decadienol compound (3: R$^1$=CH$_3$)

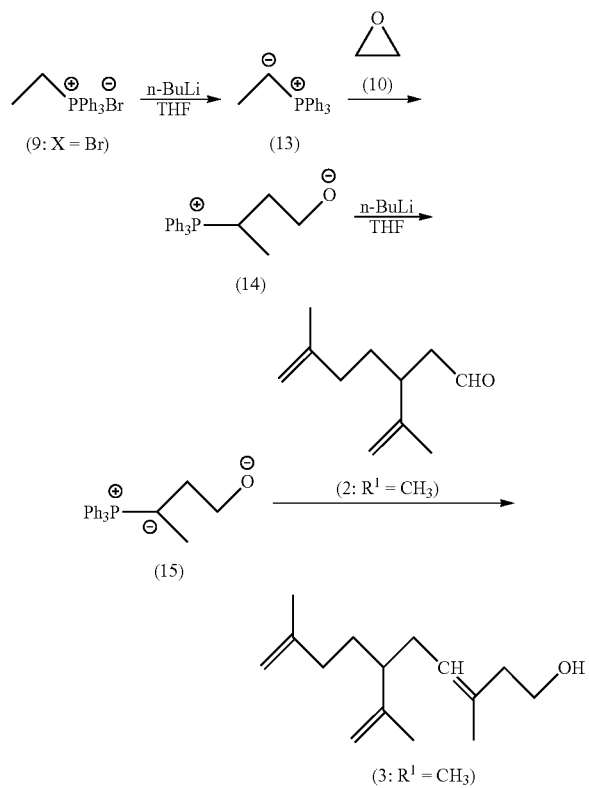

In a reactor were placed an ethyltriphenylphosphonium halide compound (9: X=Br) (5.35 g, 0.014 mol) and tetrahydrofuran (THF) (70.08 g) in a nitrogen atmosphere and cooled to 0 to 5° C. A hexane solution (5.10 ml) of n-butyl lithium (n-BuLi) (0.014 mol) was added dropwise to the reaction mixture over 8 minutes and then stirred for 15 minutes to prepare an ylide (13). Ethylene oxide (10) (0.63 g: 0.014 mol) was added dropwise to the reaction mixture over 4 minutes and then stirred at 15 to 20° C. for 1 hour to prepare 3-triphenylphosphoniobutoxide (14). The reaction mixture was cooled to −5 to 0° C., and a hexane solution (4.50 ml) of n-butyl lithium (n-BuLi) (0.013 mol) was added dropwise over 8 minutes and then stirred for 15 minutes to prepare phosphorus ylide (15). The reaction mixture was cooled to −5 to 0° C., and a 3-isopropenyl-6-heptenal compound (2: R$^1$=CH$_3$) (2.00 g: 0.011 mol) obtained as in Example 11 was added dropwise over 20 minutes. The temperature of the mixture was then raised to room temperature (20 to 25° C.) and stirred for 3 hours. Pure water (101 g) was added to the reaction mixture and stirred for 30 minutes, and the organic phase was separated. The separated organic phase was subjected to post-treatment, i.e., usual drying and concentration, and hexane (101 g) was added to the resulting solution and stirred for 30 minutes. Then, the mixture was subjected to filtration and concentration to obtain a crude product of the target compound, 6-isopropenyl-3-methyl-3,9-decadienol compound (3: R$^1$=CH$_3$) (2.89 g) in a crude yield of 67.34%.

6-Isopropenyl-3-methyl-3,9-decadienol compound (3: R$^1$=CH$_3$)
IR (D-ATR): ν=3340, 3072, 2966, 2932, 1646, 1448, 1374, 1185, 1102, 1043, 1005, 887 cm-1.
$^1$H-NMR (500 MHz, CDCl$_3$): δ=1.37-1.54 (3H, m), 1.60-1.71 (9H, m), 1.84-2.14 (5H, m), 2.21-2.34 (2H, m), 3.59-3.67 (2H, m), 4.64-4.77 (4H, m), 5.14-5.28 (1H, m) ppm.
$^{13}$C-NMR (125 MHz, CDCl$_3$): δ=15.77, 18.02, 18.49, 22.48, 22.50, 23.35, 30.75, 30.85, 32.04, 32.13, 35.18, 35.49, 35.52, 42.62, 47.34, 59.64, 60.53, 109.56, 109.63, 111.65, 111.81, 126.79, 126.98, 131.48, 131.50, 145.99, 146.09, 147.22, 147.52 ppm.
GC-MS (EI, 70 eV): 29, 41, 55, 69, 81, 93, 107, 121, 133, 149, 163, 177, 191, 207, 222.

Example 14: Synthesis of a 6-isopropenyl-3-methyl-3,9-decadienyl carboxylate Compound (4: R$^1$=H, R$^3$=CH$_3$)

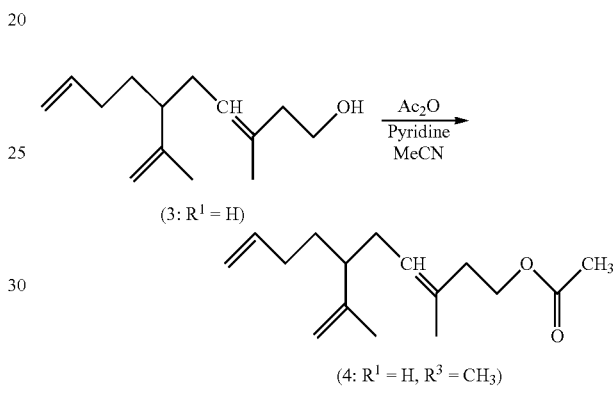

In a reactor were placed a 6-isopropenyl-3-methyl-3,9-decadienol compound (3: R$^1$=H) (1.84 g: 0.009 mol) obtained as in Example 12, acetic anhydride (Ac$_2$O) (1.54 g: 0.013 mol), pyridine (2.49 g: 0.031 mol), and acetonitrile (MeCN) (1.84 g) in a nitrogen atmosphere and stirred at room temperature (20 to 25° C.) for 18 hours. Pure water (10 g) and hexane (10 g) were added to the reaction mixture and stirred for 30 minutes, and the organic phase was separated. The separated organic phase was subjected to post-treatment, i.e., usual washing, drying, and concentration, to obtain a crude product of the target compound, 6-isopropenyl-3-methyl-3,9-decadienyl carboxylate compound (4: R$^1$=H, R$^2$=CH$_3$) (2.13 g). The crude product was subjected to distillation at a reduced pressure to obtain a purified 6-isopropenyl-3-methyl-3,9-decadienyl carboxylate compound (4: R$^1$=H, R$^3$=CH$_3$) (8) (1.68 g: 0.007 mol) in a post-distillation yield of 77.78%.

6-Isopropenyl-3-methyl-3,9-decadienyl carboxylate compound (4: R$^1$=H, R$^3$=CH$_3$)
IR (D-ATR): ν=3074, 2968, 2926, 1742, 1642, 1442, 1364, 1237, 1041, 995, 909, 890 cm-1.
$^1$H-NMR (500 MHz, CDCl$_3$): δ=1.36-1.50 (2H, m), 1.60-1.72 (6H, m), 1.88-2.10 (8H, m), 2.21-2.36 (2H, m), 4.07-4.13 (2H, m), 4.66-4.77 (2H, m), 4.91-5.01 (2H, m), 5.12-5.21 (OH, m), 5.75-5.83 (OH, m) ppm.
$^{13}$C-NMR (125 MHz, CDCl$_3$): δ=16.22, 18.43, 20.99, 21.03, 23.57, 31.24, 31.59, 31.90, 31.97, 32.13, 38.61, 46.87, 47.04, 62.69, 63.05, 111.53, 111.67, 114.26, 114.28, 125.69, 126.41, 131.13, 131.25, 138.93, 138.96, 147.08, 147.18, 171.07, 171.11 ppm.
GC-MS (EI, 70 eV): 29, 43, 55, 67, 81, 93, 107, 121, 135, 147, 161, 175, 190, 207, 222, 235, 250.

Example 15: Synthesis of a 6-isopropenyl-3-methyl-3,9-decadienyl carboxylate Compound (4: R=CH$_3$, R$^3$=CH$_2$CH$_3$)

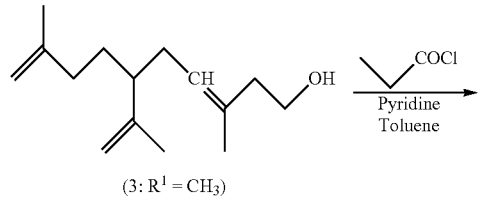

(3: R$^1$ = CH$_3$)

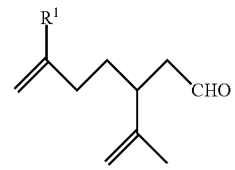

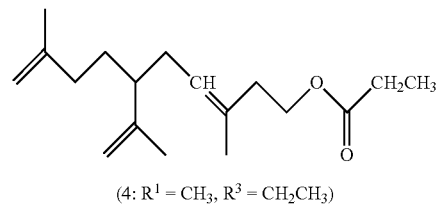

(4: R$^1$ = CH$_3$, R$^3$ = CH$_2$CH$_3$)

In a reactor were placed a 6-isopropenyl-3-methyl-3,9-decadienol compound (3: R$^1$=CH$_3$) (1.10 g: 0.005 mol) obtained as in Example 13, pyridine (0.95 g: 0.012 mol), and toluene (1.10 g) in a nitrogen atmosphere, and propionyl chloride (0.58 g, 0.063 mol) was added dropwise at an internal temperature of 0 to 10° C. over 2 minutes and stirred for 3 hours. A mixture of sodium bicarbonate (0.07 g) and pure water (2 g) was added to the reaction mixture and stirred for 30 minutes, and the organic phase was separated. The separated organic phase was subjected to post-treatment, i.e., usual washing, drying, and concentration, to obtain a crude product of the target compound, 6-isopropenyl-3-methyl-3,9-decadienyl carboxylate compound (4: R$^1$=CH$_3$, R$^3$=CH$_2$CH$_3$) (1.37 g). The crude product was purified by a column to obtain a purified 6-isopropenyl-3-methyl-3,9-decadienyl carboxylate compound (4: R$^1$=CH$_3$, R$^2$=CH$_2$CH$_3$) (1.33 g: 0.005 mol) in a post-purification yield of 96.00%.

6-Isopropenyl-3-methyl-3,9-decadienyl carboxylate compound (4: R$^1$=CH$_3$, R$^3$=CH$_2$CH$_3$)

IR (D-ATR): ν=3073, 2968, 2935, 1740, 1646, 1450, 1375, 1348, 1182, 1084, 887 cm-1.

$^1$H-NMR (500 MHz, CDCl$_3$): δ=1.12 (3H, q-like, J=7.2 Hz), 1.39-1.57 (2H, m), 1.60-1.71 (9H, m), 1.85-2.10 (5H, m), 2.27-2.36 (2H, m), 4.64-4.74 (4H, m), 5.12-5.21 (1H, m) ppm.

$^{13}$C-NMR (125 MHz, CDCl$_3$): δ=9.09, 9.12, 16.24, 18.46, 22.51, 23.57, 27.57, 30.65, 30.71, 31.28, 32.01, 32.15, 35.51, 38.68, 47.06, 47.23, 62.55, 62.92, 109.54, 109.57, 111.48, 111.62, 125.67, 126.35, 131.21, 131.34, 146.09, 147.16, 147.27, 174.43, 174.45 ppm.

GC-MS (EI, 70 eV): 29, 41, 57, 81, 107, 121, 133, 148, 175, 189, 204, 222, 249, 263, 278.

The invention claimed is:

1. A process for preparing a 3-isopropenyl-6-heptenal compound of the following formula (2):

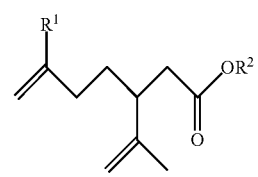

(2)

wherein R$^1$ represents a hydrogen atom or a methyl group, the process comprising:
subjecting a 3-isopropenyl-6-heptenoate ester compound of the following formula (1):

(1)

wherein R$^1$ is as defined above, and R$^2$ represents a monovalent hydrocarbon group having 1 to 10 carbon atoms, to a reduction reaction with a reducing agent to form the 3-isopropenyl-6-heptenal compound (2), wherein the reducing agent is selected from a group consisting of a complex hydride, an alkoxy derivative of the complex hydride, and an alkyl derivative of the complex hydride.

2. A process for preparing a 6-isopropenyl-3-methyl-3,9-decadienyl carboxylate compound of the following formula (4):

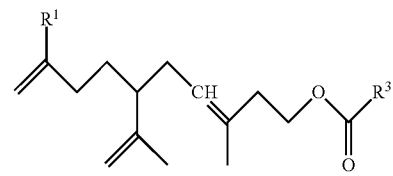

(4)

wherein R$^1$ represents a hydrogen atom or a methyl group, and R$^3$ represents a hydrogen atom or a monovalent hydrocarbon group having 1 to 10 carbon atoms, the process comprising:
the process for preparing the 3-isopropenyl-6-heptenal compound (2) according to claim 1;
subjecting the 3-isopropenyl-6-heptenal compound (2) thus obtained to a four-carbon homologation reaction including a Wittig reaction, using an ethyltriphenylphosphonium halide compound and ethylene oxide to form a 6-isopropenyl-3-methyl-3,9-decadienol compound of the following formula (3):

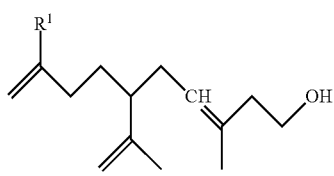
(3)

wherein R¹ is as defined above; and subjecting the 6-isopropenyl-3-methyl-3,9-decadienol compound (3) thus obtained to an esterification reaction to form the 6-isopropenyl-3-methyl-3,9-decadienyl carboxylate compound (4).

3. The process for preparing the 3-isopropenyl-6-heptenal compound (2) according to claim 1, the process further comprising:

subjecting a 4-pentenyltriphenylphosphonium halide compound of the following formula (5):

(5)

wherein R¹ is as defined above, Ph represents a phenyl group, and X represents a halogen atom, to a Wittig reaction with a 2-propanone compound of the following formula (6) having a protected hydroxyl group:

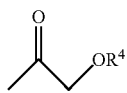
(6)

wherein R⁴ represents a protective group for a hydroxyl group, to form a 2-methyl-2,6-heptadiene compound of the following formula (7) having a protected hydroxyl group at position 1:

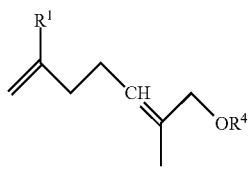
(7)

wherein R¹ and R⁴ are as defined above;

removing the protective group from the 2-methyl-2,6-heptadiene compound (7) having a protected hydroxyl group at position 1 to form a 2-methyl-2,6-heptadienol compound of the following formula (8):

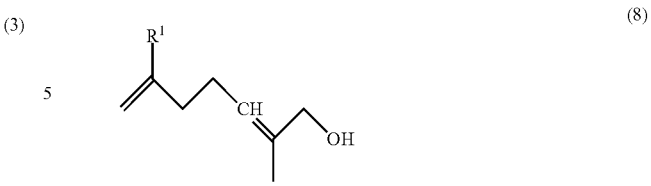
(8)

wherein R¹ is as defined above; and subjecting the 2-methyl-2,6-heptadienol compound (8) thus obtained to a Johnson-Claisen rearrangement with an orthoacetate ester compound to form the 3-isopropenyl-6-heptenoate ester compound (1).

4. The process for preparing the 3-isopropenyl-6-heptenal compound (2) according to claim 1, the process further comprising:

subjecting a 4-pentenyltriphenylphosphonium halide compound of the following formula (5):

(5)

wherein R¹ represents a hydrogen atom or a methyl group, Ph represents a phenyl group, and X represents a halogen atom, to a Wittig reaction with a 2-propanone compound of the following formula (6) having a protected hydroxyl group:

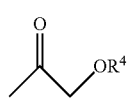
(6)

wherein R⁴ represents a protective group for a hydroxyl group, followed by removal of the protective group to form a 2-methyl-2,6-heptadienol compound of the following formula (8):

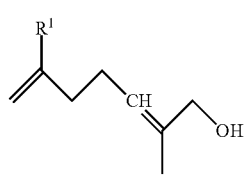
(8)

wherein R¹ is as defined above; and subjecting the 2-methyl-2,6-heptadienol compound (8) thus obtained to a Johnson-Claisen rearrangement with an orthoacetate ester compound to form the 3-isopropenyl-6-heptenoate ester compound (1).

5. The process for preparing the 6-isopropenyl-3-methyl-3,9-decadienyl carboxylate compound (4) according to claim 2, the process further comprising:

subjecting a 4-pentenyltriphenylphosphonium halide compound of the following formula (5):

(5)

wherein R¹ represents a hydrogen atom or a methyl group, Ph represents a phenyl group, and X represents a halogen atom, to a Wittig reaction with a 2-propanone compound of the following formula (6) having a protected hydroxyl group:

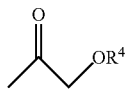

(6)

wherein R⁴ represents a protective group for a hydroxyl group,
to form a 2-methyl-2,6-heptadiene compound of the following formula (7) having a protected hydroxyl group at position 1:

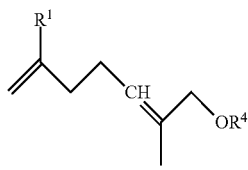

(7)

wherein R¹ and R⁴ are as defined above;
removing the protective group from the 2-methyl-2,6-heptadiene compound (7) having a protected hydroxyl group at position 1 to form a 2-methyl-2,6-heptadienol compound of the following formula (8):

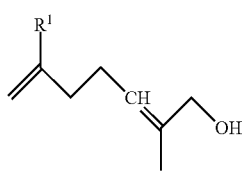

(8)

wherein R¹ is as defined above;
subjecting the 2-methyl-2,6-heptadienol compound (8) thus obtained to a Johnson-Claisen rearrangement with an orthoacetate ester compound to form the 3-isopropenyl-6-heptenoate ester compound (1).

6. The process for preparing a 6-isopropenyl-3-methyl-3,9-decadienyl carboxylate compound (4) according to claim 2, the process further comprising:
subjecting a 4-pentenyltriphenylphosphonium halide compound of the following formula (5):

(5)

wherein R¹ represents a hydrogen atom or a methyl group, Ph represents a phenyl group, and X represents a halogen atom, to a Wittig reaction with a 2-propanone compound of the following formula (6) having a protected hydroxyl group:

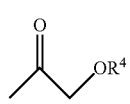

(6)

wherein R⁴ represents a protective group for a hydroxyl group,
followed by removal of the protective group to form a 2-methyl-2,6-heptadienol compound of the following formula (8):

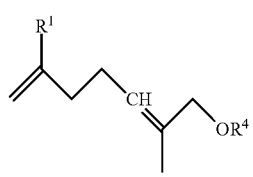

(8)

wherein R¹ is as defined above; and
subjecting the 2-methyl-2,6-heptadienol compound (8) thus obtained to a Johnson-Claisen rearrangement with an orthoacetate ester compound to form the 3-isopropenyl-6-heptenoate ester compound (1).

7. A process for preparing a 3-isopropenyl-6-heptenoate ester compound of the following formula (1):

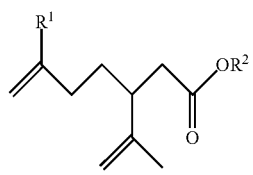

(1)

wherein R¹ represents a hydrogen atom or a methyl group, and R² represents a monovalent hydrocarbon group having 1 to 10 carbon atoms,
the process comprising:
subjecting a 4-pentenyltriphenylphosphonium halide compound of the following formula (5):

(5)

wherein R¹ is as defined above, Ph represents a phenyl group, and X represents a halogen atom, to a Wittig reaction with a 2-propanone compound of the following formula (6) having a protected hydroxyl group:

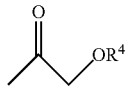
(6)

Which R⁴ represents a protective group for a hydroxyl group,
to form a 2-methyl-2,6-heptadiene compound of the following formula (7) having a protected hydroxyl group at position 1:

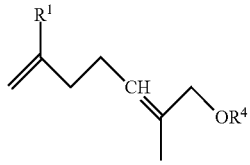
(7)

wherein R¹ and R⁴ are as defined above;
removing the protective group from the 2-methyl-2,6-heptadiene compound (7) having a protected hydroxyl group at position 1 to form a 2-methyl-2,6-heptadienol compound of the following formula (8):

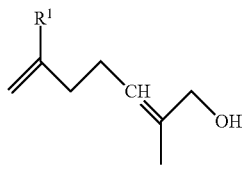
(8)

wherein R¹ is as defined above; and
subjecting the 2-methyl-2,6-heptadienol compound (8) thus obtained to a Johnson-Claisen rearrangement with an orthoacetate ester compound to form the 3-isopropenyl-6-heptenoate ester compound (1).

8. A 3-isopropenyl-6-methyl-6-heptenoate ester compound of the following general formula (1'):

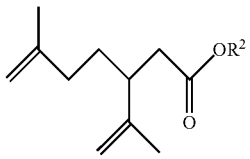
(1')

wherein R² represents a monovalent hydrocarbon group having 1 to 10 carbon atoms.

9. The process according to claim 1, wherein the reducing agent is selected from a group consisting of sodium borohydride, lithium borohydride, potassium borohydride, calcium borohydride, sodium aluminum hydride, sodium diisobutylalkoxy aluminum hydride, potassium diisobutylalkoxy aluminum hydride, lithium diisobutylalkoxy aluminum hydride, lithium aluminum hydride, sodium trimethoxy borohydride, lithium trimethoxy aluminum hydride, lithium diethoxy aluminum hydride, lithium tri-t-butoxy aluminum hydride, sodium bis(2-methoxyethoxy) aluminum hydride, lithium triethyl borohydride, aluminum diisobutyl hydride, and diisobutylalkoxy hydride.

10. The process according to claim 1, wherein the reducing agent is selected from a group consisting of aluminum diisobutyl hydride, sodium diisobutylalkoxy aluminum hydride, potassium diisobutylalkoxy aluminum hydride, and lithium diisobutylalkoxy aluminum hydride.

11. The process according to claim 1, wherein the reducing agent is selected from a group consisting of sodium diisobutylalkoxy aluminum hydride, potassium diisobutylalkoxy aluminum hydride, and lithium diisobutylalkoxy aluminum hydride and is prepared in situ in a reaction system.

12. The process according to claim 1, wherein the reducing agent is selected from a group consisting of sodium diisobutyl t-butoxy aluminum hydride, potassium diisobutyl t-butoxy aluminum hydride, and lithium diisobutyl t-butoxy aluminum hydride.

\* \* \* \* \*

UNITED STATES PATENT AND TRADEMARK OFFICE
CERTIFICATE OF CORRECTION

PATENT NO. : 11,807,602 B2
APPLICATION NO. : 17/543877
DATED : November 7, 2023
INVENTOR(S) : Baba et al.

It is certified that error appears in the above-identified patent and that said Letters Patent is hereby corrected as shown below:

In the Specification

Column 20, Lines 10-15, Formula (14): Please delete the formula and replace with the following:

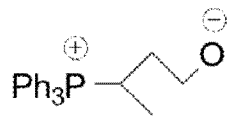

(14)

Column 20, Lines 22-25, Formula (15): Please delete the formula and replace with the following:

(15)

Column 20, Line 35: Please insert the following phrase: --Reaction Route 2--

Column 20, Lines 59-67, Formula (17): Please delete the formula and replace with the following:

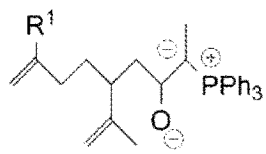

(17)

Signed and Sealed this
Second Day of April, 2024

Katherine Kelly Vidal
*Director of the United States Patent and Trademark Office*

Column 39, Lines 51-52: Please correct "product]+[(weight" to read --product]÷[(weight--

Column 40, Line 45: Please correct "642 cm-1" to read --642 $cm^{-1}$--

Column 41, Line 49: Please correct "685 cm-1" to read --685 $cm^{-1}$--

Column 41, Line 52: Please correct "OH, t-like" to read --1H, t-like--

Column 41, Line 52: Please correct "(OH, m)" to read --(1H, m)--

Column 42, Line 56: Please correct "912 cm-1" to read --912 $cm^{-1}$--

Column 42, Line 59: Please correct "OH, q" to read --1H, q--

Column 42, Line 60: Please correct "(OH, m)" to read --(1H, m)--

Column 42, Line 61: Please correct "(OH, m)" to read --(1H, m)--

Column 43, Line 62: Please correct "886 cm-1" to read --886 $cm^{-1}$--

Column 44, Lines 48-49: Please correct "641 cm-1" to read --641 $cm^{-1}$--

Column 44, Line 52: Please correct "(OH, m)" to read --(1H, m)--

Column 46, Line 3: Please correct "887 cm-1" to read --887 $cm^{-1}$--

Column 46, Lines 14-15: Please correct "(1: $R^1$=H, $R^2$=" to read --(1: $R^1$=H, $R^2$=Et)--

Column 46, Lines 56-57: Please correct "559 cm-1" to read --559 $cm^{-1}$--

Column 47, Lines 2-3: Please correct "(1: $R^1$=$CH_3$, $R^2$" to read --(1: $R^1$=$CH_3$, $R^2$=Et)--

Column 47, Line 56: Please correct "889 cm-1" to read --889 $cm^{-1}$--

Column 48, Line 43: Please correct "897 cm-1" to read --897 $cm^{-1}$--

Column 49, Line 37: Please correct "890 cm-1" to read --890 $cm^{-1}$--

Column 50, Line 55: Please correct "559 cm-1" to read --559 $cm^{-1}$--

Column 52, Line 4: Please correct "887 cm-1" to read --887 $cm^{-1}$--

Column 52, Line 56: Please correct "890 cm-1" to read --890 $cm^{-1}$--

Column 52, Line 60: Please correct "5.12-5.21 (OH, m), 5.75-5.83 (OH, m)" to read --5.12-5.21 (1H, m), 5.75-5.83 (1H, m)--

CERTIFICATE OF CORRECTION (continued)
U.S. Pat. No. 11,807,602 B2

Column 53, Lines 2-3: Please correct "(4: R=CH$_3$, R$^3$=CH$_2$CH$_3$)" to read --(4: R$^1$=CH$_3$, R$^3$=CH$_2$CH$_3$)--

Column 53, Line 50: Please correct "887 cm-l" to read --887 cm$^{-1}$--

In the Claims

Column 59, Line 12, Claim 7: Please correct "Which" to read --wherein--